(12) United States Patent
Wegener et al.

(10) Patent No.: US 8,795,180 B2
(45) Date of Patent: *Aug. 5, 2014

(54) ULTRASOUND SIGNAL COMPRESSION

(75) Inventors: Albert W. Wegener, Aptos Hills, CA (US); Michael V Nanevicz, Palo Alto, CA (US)

(73) Assignee: Altera Corporation, San Jose, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 13/408,174

(22) Filed: Feb. 29, 2012

(65) Prior Publication Data

US 2012/0157852 A1 Jun. 21, 2012

Related U.S. Application Data

(62) Division of application No. 12/477,062, filed on Jun. 2, 2009, now Pat. No. 8,157,738.

(51) Int. Cl.
*A61B 8/00* (2006.01)
*G01S 7/52* (2006.01)
*A61B 8/08* (2006.01)

(52) U.S. Cl.
CPC ............. *G01S 7/52034* (2013.01); *A61B 8/483* (2013.01)
USPC .......................................... 600/443; 600/437

(58) Field of Classification Search
USPC .................... 600/437, 443, 459; 367/103, 104
See application file for complete search history.

(56) References Cited

U.S. PATENT DOCUMENTS

| | | | |
|---|---|---|---|
| 4,751,929 A | 6/1988 | Hayakawa et al. | |
| 6,042,545 A | 3/2000 | Hossack et al. | |
| 6,315,722 B1 | 11/2001 | Yaegashi | |
| 6,855,113 B2 | 2/2005 | Amemiya et al. | |
| 7,009,533 B1 | 3/2006 | Wegener | |
| 7,088,276 B1 | 8/2006 | Wegener | |
| 7,642,939 B2 * | 1/2010 | Nanevicz | ...................... 341/101 |

(Continued)

FOREIGN PATENT DOCUMENTS

| | | |
|---|---|---|
| JP | 11347033 A | 12/1999 |
| JP | 2005081082 | 3/2005 |

(Continued)

OTHER PUBLICATIONS

Ali, Murtaza, et al., "Signal Processing Overview of Ultrasound Systems for Medical Imaging," Texas Instruments White Paper SPRAB12, Nov. 2008, 26 pages.

(Continued)

*Primary Examiner* — Michael Rozanski
(74) *Attorney, Agent, or Firm* — Okamoto & Benedicto LLP

(57) ABSTRACT

A method and an apparatus for an ultrasound system provide compression of ultrasound signal samples after analog to digital conversion and before beamforming. The analog ultrasound signals received from an array of ultrasound transducer elements are digitally sampled by a plurality of analog to digital converters (ADCs) to produce a plurality of sequences of signal samples. Each sequence of signal samples is compressed to form a corresponding sequence of compressed samples. The resulting sequences of compressed samples are transferred via a digital interface to an ultrasound signal processor. At the ultrasound signal processor, the received sequences of compressed samples are decompressed. The typical processing operations, such as beamforming, downconversion and detection, are applied to decompressed samples. This abstract does not limit the scope of the invention as described in the claims.

4 Claims, 26 Drawing Sheets

(56) References Cited

U.S. PATENT DOCUMENTS

| | | | |
|---|---|---|---|
| 7,973,682 B2 * | 7/2011 | Nanevicz | 341/101 |
| 2003/0149362 A1 | 8/2003 | Azuma et al. | |
| 2005/0124890 A1 | 6/2005 | Halmann et al. | |
| 2005/0148878 A1 | 7/2005 | Phelps et al. | |
| 2006/0074320 A1 | 4/2006 | Yoo et al. | |
| 2007/0239019 A1 | 10/2007 | Richard et al. | |
| 2008/0114246 A1 | 5/2008 | Randall et al. | |
| 2009/0284401 A1 | 11/2009 | Nanevicz | |

FOREIGN PATENT DOCUMENTS

| | | |
|---|---|---|
| WO | 9709930 | 3/1997 |
| WO | 0010638 A2 | 3/2000 |
| WO | 0030544 A1 | 6/2000 |

OTHER PUBLICATIONS

Behar, V., et al., "Parameter optimization of pulse compression in ultrasound imaging system with coded excitation," Ultrasonics, vol. 42 (2004) pp. 1101-1109.

Delgorge, et al., "A Tele-Operated Mobile Ultrasound Scanner Using a Light-Weight Robot," IEEE Trans. Information Technology in Biomedicine, vol. 9, No. 1, Mar. 2005, pp. 50-58.

Delgorge, et al., "Comparative Survey of Ultrasound Images Compression Methods Dedicated to a Tele-Echography Robotic System," 2001 Proc. 23rd Annual IEEE Engineering in Medicine and Biology Society Intl. Conf. pp. 2461-2464.

Gupta, et al., "Despeckling of Medical Ultrasound Images Using Data and Rate Adaptive Lossy Compression," IEEE Trans. Medical Imaging, vol. 24, No. 6, Jun. 2005, pp. 743-754.

Li, et al., "A Novel B-Mode Ultrasound Image Compression Method Based on Beam Forming Data," 1998 Proc. Intl. Conf. IEEE Engineering in Medicine and Biology Society, vol. 20, No. 3, pp. 1274-1276.

LVDS Owner's Manual Including High-Speed CML and Signal Conditioning, 4th Edition, Jan. 2008, National Semiconductor, 116 pages.

Reutsch, G., et al., "Getting Started with CUDA," Nvidia Corp., 2008, 65 pages.

Seiler et al., "Larrabee: A Many-Core x86 Architecture for Visual Computing," ACM Transactions on Graphics, vol. 27, No. 3, Article 18, Aug. 2008, 16 pages.

Strintzis, et al., "Maximum Likelihood Motion Estimation in Ultrasound Image Sequences," IEEE Signal Processing Letters, vol. 4, No. 6, Jun. 1997, pp. 156-157.

PCT Search Report Mailed Jan. 3, 2011 in PCT/US2010/036672, 8 pages.

PCT Search Report Mailed Jan. 26, 2011 in PCT/US2010/039081, 8 pages.

* cited by examiner

| n_exp | n_LSB | m_exp |
|---|---|---|
| 0 | 0 | 0 |
| 2 | 0 | 2 |
| 3 | 0 | 3 |
| 4 | 1 | 3 |
| 5 | 1 | 4 |
| 6 | 1 | 5 |
| 7 | 1 | 6 |
| 8 | 2 | 6 |
| 9 | 2 | 7 |
| 10 | 2 | 8 |
| 11 | 2 | 9 |
| 12 | 3 | 9 |
| 13 | 3 | 10 |
| 14 | 4 | 10 |

Figure 15

| Center Frequency | Frequency Band Indicator | Demux Control x(i), x(i-j) | Inverter Control | Modified Sample |
|---|---|---|---|---|
| DC | 1 | x(i), x(i-1) | on = -x(i-1) | y(i) = x(i) - x(i-1) |
| fs/6 | 2 | x(i), x(i-3) | off | y(i) = x(i) + x(i-3) |
| fs/4 | 3 | x(i), x(i-2) | off | y(i) = x(i) + x(i-2) |
| fs/3 | 4 | x(i), x(i-3) | on = -x(i-3) | y(i) = x(i) - x(i-3) |
| fs/2 | 5 | x(i), x(i-1) | off | y(i) = x(i) + x(i-1) |

Figure 21

| Band | Center Freq. | Modified Sample | Example Differences or Sums |
|---|---|---|---|
| 1 | DC | $y(i) = x(i) - x(i-1)$ | 912 →<br>x(i): 32767 32702 32508 32186 31737 31163 30465 29648<br>x(i-1): 32767 32702 32508 32186 31737 31163 30465 29648<br>DIFF: -65 -194 -322 -449 -574 -707 -781 -935<br>922 → |
| 2 | $f_s/6$ | $y(i) = x(i) + x(i-3)$ | x(i): 32767 16628 -15890 -32756 -17356 -15140 32722 18071<br>x(i-3): --- --- --- 32767 16628 -15890 -32756 -17356<br>SUM: --- --- --- 11 -728 -750 -34 715<br>932 → |
| 3 | $f_s/4$ | $y(i) = x(i) + x(i-2)$ | x(i): 32767 -389 -32758 1166 32730 -1944 -32684 2719 32619<br>x(i-2): --- 32767 -389 -32758 1166 32730 -1944 -32684<br>SUM: --- 9 777 -778 28 46 775 -65<br>942 → |
| 4 | $f_s/3$ | $y(i) = x(i) - x(i-3)$ | x(i): 32767 -15792 -17546 32703 -13977 -19233 32513 -12107 -20845<br>x(i-3): --- --- --- 32767 -15792 -17546 32703 -13977 -19233<br>DIFF: --- --- --- -64 1815 -1687 -190 1870 -1612<br>952 → |
| 5 | $f_s/2$ | $y(i) = x(i) + x(i-1)$ | x(i): 32767 -32671 32382 -31906 31239 -30392 29364 -28166 26801<br>x(i-1): --- 32767 -32671 32382 -31906 31239 -30392 29364 -28166<br>SUM: --- 96 -289 476 -667 847 -1028 1198 -1356 |

Figure 22

ULTRASOUND SIGNAL COMPRESSION

RELATED APPLICATIONS

This application is a divisional of U.S. patent application Ser. No. 12/477,062 filed on 2 Jun. 2009, now U.S. Pat. No. 8,157,738, which application is incorporated by reference as if fully set forth herein.

BACKGROUND OF THE INVENTION

The present invention relates to compression of ultrasound signal data received by ultrasound transducers, particularly to compressing ultrasound signal samples after analog to digital conversion and prior to beamforming, detection and image formation.

Medical ultrasound systems scan the internal anatomy of a subject by transmitting ultrasound beams from a transducer placed on the subject by a clinician. The ultrasound waves are reflected at interfaces of internal tissues having different acoustic impedances, producing echoes. The transducer receives the echoes and converts them to electrical ultrasound signals. The ultrasound system applies a sequence of processing steps to the ultrasound signals to produce an image or series of images that are displayed at a control console for analysis by the clinician. Images formed based on the strength of the received echo are referred to as B-mode images. In addition, the system can measure the Doppler shifts of the ultrasound signals to produce color images indicating the flow of fluid, such as blood, and perform additional analyses useful for diagnosis.

A conventional medical ultrasound transducer includes an array of piezoelectric elements that transmit ultrasound waves when driven by electrical signals, receive the returning echoes and convert the received echoes to a plurality of analog signals. A plurality of analog to digital converters (ADCs) sample the analog signals, each producing a stream of digital signal samples. Typical digital signal processing of the signal samples includes beamforming, downconversion, B-mode (brightness) processing and/or Doppler processing, scan-conversion and image processing for display. The beamformer delays and combines the streams of signal samples to form an array of beamformed samples corresponding to a particular direction in the field of view. The beamformer can produce a number of arrays of beamformed samples corresponding to a number of directions in the field of view. Depending on the type of diagnostic information desired, B-mode processing and/or Doppler processing are then performed on the beamformed samples to form B-mode detected samples and/or Doppler detected samples. The spatial coordinates of the detected samples still correspond to the beam geometry of the beamformed samples. The scan converter performs coordinate transformations of the detected samples to produce frames of data having a raster format appropriate for display. Additional image processing is applied to the frames of samples to allow their display as two-dimensional (2-D) or three-dimensional (3-D) images.

Current efforts for improving medical ultrasound systems are directed to increasing the diagnostic capabilities of console/cart systems and developing smaller portable devices with improved image quality. For the high-end console or cart systems, it is desirable to increase the number of transducer elements to produce higher resolution and/or 3-D images to expand the diagnostic capability. Increasing the number of transducer elements increases the amount of data communicated from the transducer head to the console processor, which can require a higher bandwidth communication channel and a larger cable connection. The data acquisition capacity of the transducer head is constrained by requirements for manipulation and form factors. Hand-carried and handheld ultrasound devices are economical and desirable for use in small clinics, mobile treatment units and the home. For these devices, battery life is also a constraint. More efficient processing, transfer and storage of ultrasound signal data in the ultrasound system can conserve power, data transfer bandwidth and memory capacity.

Compression of ultrasound signal data can provide benefits for both console/cart systems and portable systems. The benefits include reducing the data transfer bandwidth, memory capacity and power requirements of the system. For a portable or hand-carried ultrasound system, these benefits reduce weight and increase battery life. For a console system, compression mitigates the impact of increasing amounts of data acquired by the transducer head and transport of the data to the ultrasound signal processor. Compression that is computationally efficient introduces the benefits of compression with low or no impact on system complexity.

The present description uses the term "compression" to refer to data compression of ultrasound signal samples where the number of bits representing the signal samples is reduced and the signal samples are later decompressed prior to processing for display. Some descriptions of ultrasound imaging systems use the term compression to mean "pulse compression," not data compression. Pulse compression refers to filtering and/or modulation of the transmitted ultrasound pulses and inverse filtering and/or demodulation of the received ultrasound pulses. (For example, see "Parameter optimization of pulse compression in ultrasound imaging system with coded excitation," by V. Behar and D. Adam in Ultrasonics vol. 42, pp. 1101-1109, 2004.) Some descriptions of ultrasound imaging systems use the term compression to mean "log compression," not data compression. In that context, log compression refers to calculating the logarithm of processed ultrasound data, typically the magnitude detected data prior to display. (For example, see "Signal Processing Overview of Ultrasound Systems for Medical Imaging," by A. Murtaza et al., Texas Instruments SPRAB 12, pp. 1-26, Nov. 2008). Both pulse compression and log compression intentionally change characteristics of the transmitted or received ultrasound signals in the time domain and frequency domain. Data compression of the received ultrasound signal samples followed later by decompression is a process that preserves the signal characteristics in the time and frequency domains. The present description refers to lossless and lossy compression of ultrasound signal samples. In lossless compression, the decompressed samples have identical values to the original samples. In lossy compression, the decompressed samples are similar, but not identical, to the original samples. The present description uses to the term "frame" to refer to an array of ultrasound data, either raw or processed, that is eventually processed to form an ultrasound image for display. Descriptions of ultrasound imaging systems in the art also use the term "screen" to refer to a frame of ultrasound data. In the present description, "real time" means a rate that is at least as fast as the sample rate of a digital signal. The term "real time" can be used to describe rates for processing, transfer and storage of the digital signal. The sample rate is the rate at which an ADC forms samples of a digital signal during conversion of an analog signal. Some descriptions of ultrasound imaging systems in the art use the term "real time" to refer to the frame rate for display of the ultrasound images. The present description relates real time to the sample rate instead of the frame rate interpretation.

Previous applications of data compression in ultrasound systems have included alternatives for data compression before and after scan conversion for image formation. In U.S. Pat. No. 6,315,722 entitled "Ultrasonic Diagnostic Device," issued on Nov. 13, 2001, Yaegashi describes a time axis extension unit for storing ultrasound signal samples output from an ADC unit. The time axis extension unit writes the data at the rate output from the ADC unit and reads the data out at a lower rate. The time axis extension unit stores signal samples for one screen, or frame, and can be implemented using first-in first-out (FIFO) memories. A data compression unit compresses signal samples read from the time axis extension unit. Yaegashi describes applying image compression technologies, such as methods based on the discrete cosine transform (DCT) for exploiting spatial correlation within one frame of data or MPEG compression methods for multiple frames of data. (MPEG refers to the video data compression standards developed by the Moving Picture Experts Group.) The compressed samples are stored in a mass memory device, such as a hard disk. The data compression reduces the storage capacity needed in the mass memory device. For producing an image, a data expanding unit decompresses the compressed samples retrieved from the mass memory device. Conventional operations, including filtering, logarithmic conversion, detection and digital scan conversion, are applied to the decompressed samples for image formation and display. Yaegashi does not disclose beamforming in the processing sequence.

In the US Patent Publication, publication number 2008/0114246, entitled "Transducer Array Imaging System," Randall et al. describe compressing ultrasound digital data using mapping, resampling and/or data windowing before and/or after beamforming. The mapping can include requantizing or clipping signal samples. For example, the number of required bits decreases monotonically with depth so that fewer bits per sample may be assigned based on depth. In some embodiments, signal samples from receive channels extending beyond the transmit and receive apertures may be truncated. For imaging a region of interest (ROI), signal acquisition time may be proportional to depth range, so that data acquired before a minimum sample time and/or after a maximum sample time may be truncated if they do not contribute to the formation of image pixels. In some embodiments, the data may be resampled to fewer samples if the display resolution is less than required for full resolution imaging, thus reducing the number of samples transferred.

In U.S. Pat. No. 6,042,545 entitled "Medical Diagnostic Ultrasound System and Method for Transform Ultrasound Processing," issued Mar. 28, 2000, Hossack et al. describe transform compression techniques for ultrasound data after beamforming. Alternatives for beamforming include analog beamforming prior to the ADC or digital beamforming after the ADC. The beamformer generates in-phase and quadrature (I and Q) samples or, alternatively, radio frequency (RF) samples. Beamformed samples corresponding to a two-dimensional (2-D) frame are filtered and transformed to produce a transform domain representation. The transform domain samples are quantized and/or encoded for compression. The compression may be lossless or lossy. Any transform, such as the DCT or the Discrete Wavelet Transform (DWT), quantization function and encoding function may be applied for compressing the frame of data. For example, JPEG compression includes dividing the frames of data into 2-D blocks of data, transforming using a 2-D DCT on each of the blocks, quantizing the transform domain samples, differentially encoding the DC (zero frequency) transform samples between blocks, and entropy encoding the 2-D blocks of quantized transform domain samples (e.g. Huffman encoding). The JPEG compression algorithms can be configured as lossy or lossless. (JPEG compression refers to the standard image compression methods developed by the Joint Photographic Experts Group.) Additional operations in the transform domain for various image processing functions, such as filtering, are more computationally efficient in the transform domain than the spatial domain. For example, 2-D filtering in the spatial domain uses 2-D convolution operations. In the transform domain 2-D filtering uses more efficient multiplications by the transform domain filter coefficients. The compressed transform domain data can be stored for later image formation. For decompression, the inverse encoding and transform functions are applied prior to processing for display.

In the U.S. Pat. No. 6,855,113, entitled "Diagnostic Information Generation Apparatus and Ultrasonic Diagnostic System," issued Feb. 15, 2005, Amemiya et al. describe compressing frames of ultrasound data prior to wireless transmission from an ultrasonic wave unit to an information unit. The ultrasonic wave unit includes the transducer and a processer for subsequent beamforming, B-mode imaging and Doppler imaging. General purpose data compression standards are applied to the B-mode imaging data or Doppler imaging data, such as JPEG compression for a single frame or MPEG compression for multiple frames. The compressed data are transmitted using a standard wireless communication modality to the information unit. The information unit includes a central processing unit (CPU) that decompresses the received data in accordance with the compression standard. The CPU further processes the decompressed B-mode imaging data and decompressed Doppler imaging data for display.

In the PCT published application, international publication number WO 97/09930, entitled "Ultrasonic Diagnostic Apparatus for Compressing and Storing Data in CINE Memory," published Mar. 20, 1997, Lee describes compressing ultrasound data prior to storage in a CINE memory and decompressing data retrieved from the CINE memory. A CINE memory includes several banks organized by time. In this system, the ultrasonic probe performs beamforming prior to the ADC, so the ADC output data represent beamformed samples. Compression is applied to a frame of data and can be applied before or after scan conversion. The Lempel-Ziv-Welch (LZW) algorithm is applied for compression and decompression. The LZW algorithm is based on detecting repeated patterns of bits in the data and assigning codes to the repeated patterns. The compressed data for a frame retrieved from the CINE memory are decompressed and further processed for display.

In the Japanese patent application, publication number 2005-081082, entitled "Ultrasonograph and Ultrasonic Data Compression Method," published Mar. 31, 2005, Akihiro describes three embodiments for compressing ultrasound data after analog beamforming. In the first embodiment, an ADC generates I and Q samples of the analog beamformer output signals. The compressor calculates the differences between the I,Q samples of adjacent beams followed by run-length encoding of the differences to form the compressed data. The compressed data are stored in memory. Compressed data retrieved from memory are decompressed and processed for image display. In the second embodiment, an ADC generates RF samples of the analog beamformer output samples. The compressor calculates differences between the RF samples of adjacent beams followed by run-length encoding. The compressed samples are stored in memory, retrieved, decompressed and processed for image display. In the third embodiment, beamformer output is further processed to generate B-mode image frames and Doppler image frames prior to compression. The compressor calculates frame to frame differences to produce compressed data frames. The compressed data frames are stored in memory, retrieved, decompressed and further processed for display.

In the U.S. Pat. No. 4,751,929, entitled "Ultrasonic Bloodstream Diagnostic Apparatus with Dual Displays of Velocity Profiles and Average Flow Velocity," issued Jun. 21, 1988, Hayakawa et al. describe compressing Doppler frequency detected data. The compressor operates on the output of a squaring and adding circuit that calculates the magnitude squared of the real and imaginary parts of the frequency spectrum samples. The compressor re-encodes the bits of each sample output from the adder to reduce the number of bits in the representation. The compressor operates on the adder output sample to encode the location of the most significant bit in the mantissa, preserve a fixed number of most significant bits and remove the remaining least significant bits. The resulting compressed word for each sample includes the fixed number of most significant bits and a code indicating the number of least significant bits eliminated from the original sample. A variable number of least significant bits are removed from each sample, so the compression is lossy.

In the paper entitled "A Novel B-Mode Ultrasound Image Compression Method Based on Beam Forming Data," 1998 Proc. Intl. Conf. IEEE Engineering in Medicine and Biology Society, Vol. 20 No. 3, pp. 1274-76, Li et al. describe compressing beamformed samples for transmission in a tele-ultrasound system. The DWT is applied to a frame of 128×512 beamformed samples. The coefficients of subimages in the vertical direction are quantized and encoded using arithmetic coding. After decompression, scan conversion is applied to the frame of 128×512 decompressed samples to form the frame of 512×512 samples for display.

Several papers describe different methods for compressing ultrasound images after scan conversion for image formation. A few examples include the following. In the paper entitled "Comparative Survey of Ultrasound Images compression Methods Dedicated to a Tele-Echography Robotic System," 2001 Proc. 23$^{rd}$ Annual IEEE Engineering in Medicine and Biology Society Intl. Conf., pp. 2461-64, Delgorge et al. describe applying different compression methods to ultrasound images. The methods include Fourier transform, DCT, quadtree decomposition, DWT, fractals, histogram thresholding and run length coding. The methods are applied to 512× 512 ultrasound images after scan conversion. In the paper entitled "Despeckling of Medical Ultrasound Images Using Data and Rate Adaptive Lossy Compression," IEEE Trans. Medical Imaging, vol. 24, No. 6, Jun. 2005, pp. 743-54, Gupta et al. describe combining compression with an algorithm to remove speckle from the ultrasound image. The DWT is followed by the speckle removal algorithm, quantization and entropy encoding. In the paper entitled "A Tele-Operated Mobile Ultrasound Scanner Using a Light-Weight Robot," IEEE Trans. Information Technology in Biomedicine, Vol. 9, No. 1, Mar. 2005, pp. 50-58, Delgorge et al. describe applying various lossless and lossy compression methods to ultrasound images. The lossless methods include Huffman, arithmetic coding, Lempel-Ziv, run length coding and Fano coding. The lossy methods include various JPEG versions, including JPEG, JPEG-LS and JPEG2000. In the paper entitled "Maximum Likelihood Motion Estimation in Ultrasound Image Sequences," IEEE Signal Processing Letters, Vol. 4, No. 6, June 1997, pp. 156-7, Strintzis et al. describe applying MPEG compression to a sequence of ultrasound images. The method includes detecting motion vectors for 8×8 blocks of pixels between consecutive frames in the sequence of images. The motion vectors are encoded for frame to frame MPEG compression.

The commonly owned U.S. Pat. No. 7,009,533 (the '533 patent), entitled "Adaptive Compression and Decompression of Bandlimited Signals", dated Mar. 7, 2006, describes algorithms for compression and decompression of certain bandlimited signals. The commonly owned U.S. Pat. No. 7,088,276 (the '276 patent), entitled "Enhanced Data Converters Using Compression and Decompression," dated Aug. 8, 2007, describes applying lossless or lossy compression to signal samples output from an ADC implemented in a single integrated circuit. The commonly owned and copending U.S. patent application Ser. No. 12/120,988 (the '988 application), filed May 15, 2008, entitled "Digital Interface for Data Converters," describes multiplexing data output from multiple ADCs in parallel to reduce the number of active data ports at the digital interface.

There is a need for efficient data transfer and storage of ultrasound signal data between components of the ultrasound imaging system. There is a need for computationally efficient data compression of ultrasound signal data to improve data transfer and storage capacity with minimal impact on system complexity.

SUMMARY OF THE INVENTION

Embodiments of the present invention have been made in consideration of the foregoing conventional problems. An object of the present invention is to compress ultrasound signal samples after analog to digital conversion in an ultrasound imaging system. The ultrasound imaging system includes an array of ultrasound transducer elements that outputs a plurality of analog ultrasound signals during a sampling window. The method comprises:

digitally sampling the plurality of analog ultrasound signals using analog to digital converters to produce a plurality of sequences of signal samples, each sequence of signal samples representing an analog ultrasound signal output by a corresponding transducer element during the sampling window;

compressing the plurality of sequences of signal samples to form a plurality of corresponding sequences of compressed samples, including compressing a particular sequence of signal samples in the plurality of sequences of signal samples independently from signal samples representing analog ultrasound signals output from other transducer elements during said sampling window to form the corresponding sequence of compressed samples; and transferring the plurality of corresponding sequences of compressed samples across a data transfer interface to a signal processor.

The compressed samples are decompressed prior to beamforming or other ultrasound signal processing operations.

Another object of the present invention is to provide an apparatus to compress ultrasound signal samples after analog to digital conversion of analog ultrasound signals in an ultrasound imaging system. The ultrasound imaging system includes an array of ultrasound transducer elements that outputs a plurality of analog ultrasound signals during a sampling window. The apparatus comprises an integrated circuit device having a plurality of analog inputs for receiving the plurality of analog ultrasound signals and a plurality of data ports at a digital interface, the integrated circuit device comprising:

a plurality of ADCs coupled to digitally sample the plurality of analog ultrasound signals received at the analog inputs to produce a plurality of sequences of signal samples during the sampling window, each ADC sampling a corresponding analog ultrasound signal output by a corresponding transducer element to form a corresponding sequence of signal samples; and a compressor having multiple inputs coupled to receive the plurality of sequences of signal samples and producing a plurality of sequences of compressed samples, the compressor including a plurality of compression units, wherein a corresponding compression unit compresses the corresponding sequence of signal samples independently from signal samples representing analog ultrasound signals output from other transducer elements during said sampling window to form a corresponding sequence of compressed samples, wherein the plurality of sequences of compressed samples are provided to the plurality of data ports for transfer over the digital interface to the signal processor.

Another aspect of the present invention exploits excess data transfer bandwidth of the data ports to use fewer data ports to transfer the compressed samples over the digital interface. The sequences of compressed samples can be multiplexed to form fewer sequences that can be transferred using fewer data ports.

Another aspect of the present invention exploits excess data transfer bandwidth of the data ports to use fewer data ports to transfer uncompressed ultrasound signal samples over the digital interface. When the bit rates of the signal samples output from the plurality of ADCs are sufficiently less than the maximum data transfer bandwidth of the data ports, the sequences of uncompressed signal samples can be multiplexed to form fewer sequences that can be transferred using fewer data ports.

BRIEF DESCRIPTION OF THE DRAWINGS

FIG. 15 is a table of exemplary values of n_exp, n_LSB and m_exp.

FIG. 21 shows the operations that produce modified samples based on the center frequency.

FIG. 22 gives the sums or differences of signal samples x(i) and x(i-j) for the examples of FIG. 19.

DETAILED DESCRIPTION

Figure 1:
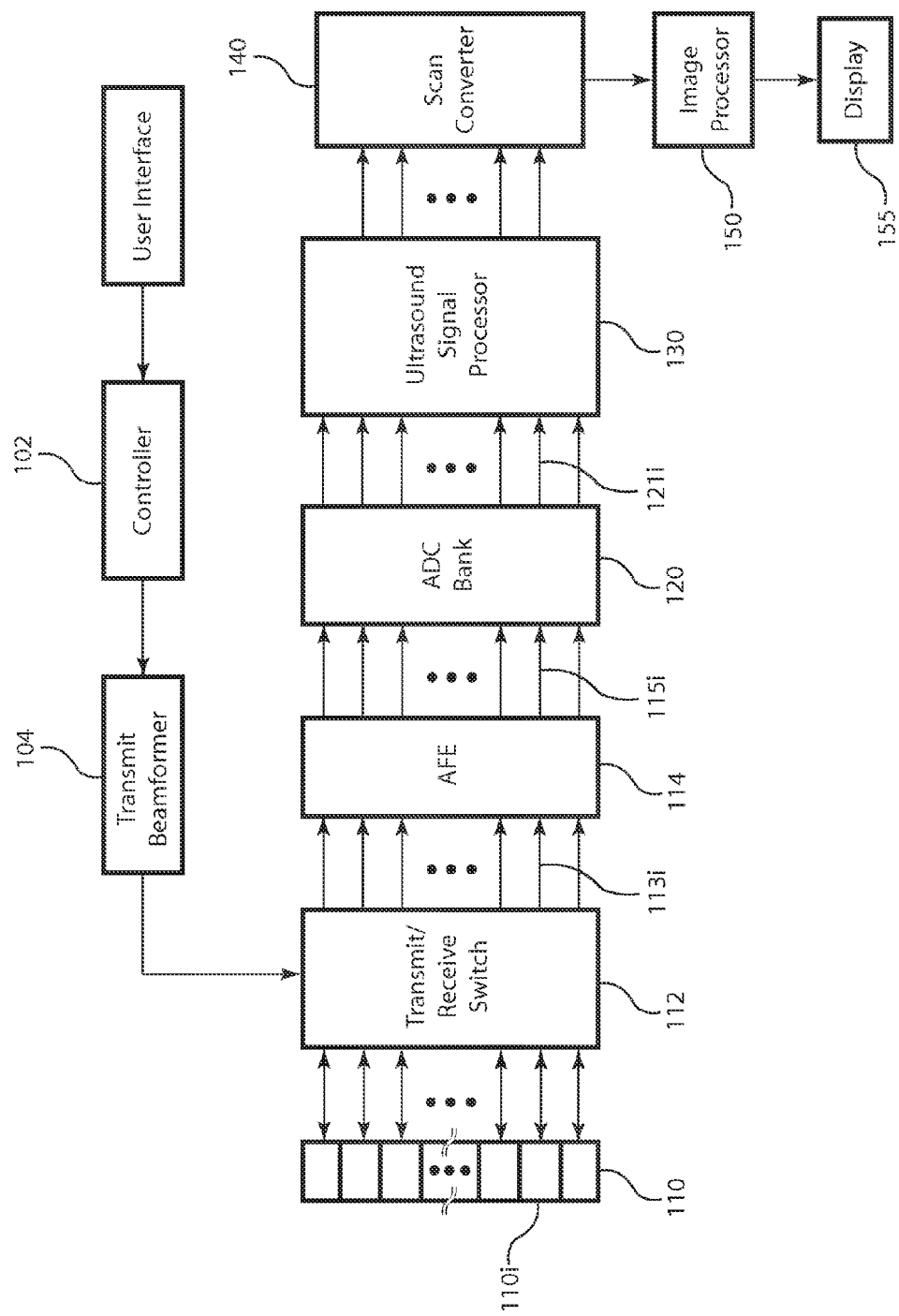
FIG. 1 is a block diagram of an example of a typical medical ultrasound system in accordance with the prior art.

FIG. 1 is a block diagram of an example of a typical medical ultrasound system in accordance with the prior art. The transmit beamformer 104 is of a construction known in the art, such as a digital or analog beamformer. The transmit beamformer 104 generates one or more excitation signals in response to the system controller 102. The excitation signal has an associated center frequency, typically in the 1 to 20 MHz range. The excitation signals from the transmit beamformer 104 are provided to the ultrasound transducer 110 via the transmit/receive switch 112. The ultrasound transducer 110 comprises an array of transducer elements 110i. The ultrasound transducer 110 is of a construction known in the art that enables the coupling the ultrasound waves to the subject being examined. The transducer elements 110i both launch and receive ultrasound waves. The transmit/receive switch 112 includes the switching circuitry for transmit and receive modes. For transmit mode, the transmit/receive switch 112 couples the excitation signals from the transmit beamformer 104 to the transducer 110. For receive mode, the transmit/receive switch 112 couples the received ultrasound signals from the transducer 110 to the analog front end (AFE) 114. For transmission, the transducer elements 110i convert the excitation signals to produce ultrasonic acoustic waveforms. In particular, the transducer 110 converts the excitation signals into ultrasound waveforms that travel in directions within the subject in response to the transmit beamformer 104. Scattering sites having interfaces with different acoustic impedances reflect the ultrasonic waveforms, causing echoes to be returned to the transducer 110. The plurality of transducer elements 110i receives the echoes and converts them to a plurality of analog ultrasound signals. The transmit/receive switch 112 couples the plurality of analog ultrasound signals from the transducer 110 to the AFE 114 during a sampling window. The sampling window corresponds to an interval of time during which the received echoes represent reflections from scattering sites within a desired depth range in the subject. The controller 102 sets the sampling window in accordance with user input or a scan protocol and provides the timing control information to the transmit/receive switch 112. The transmit/receive switch 112 outputs the plurality of analog ultrasound signals in parallel during the sampling window. The AFE 114 amplifies and filters the plurality of analog ultrasound signals in preparation for analog to digital conversion. The AFE 114 can include a low noise amplifier (LNA), a variable gain amplifier (VGA) and a lowpass filter for each analog signal channel 113i. The VGA applies a gain profile that increases gain as a function of time, since the received signal strength decreases with time. The decrease in signal strength with time results from the attenuation of the ultrasound wave as it travels a longer path through more tissue. The ADC bank 120 includes a plurality of ADCs to convert the plurality of analog ultrasound signals received during the sampling window to a plurality of sequences of ultrasound signal samples in parallel. The analog ultrasound signal at each ADC input channel 115i is converted to a stream of ultrasound signal samples at the corresponding ADC output channel 121i. The ultrasound signal samples have a non-zero center frequency, typically corresponding to the radio frequency (RF) of the received ultrasound signals related to the natural, resonant frequency of the piezoelectric material of the transducer.

Figure 2:
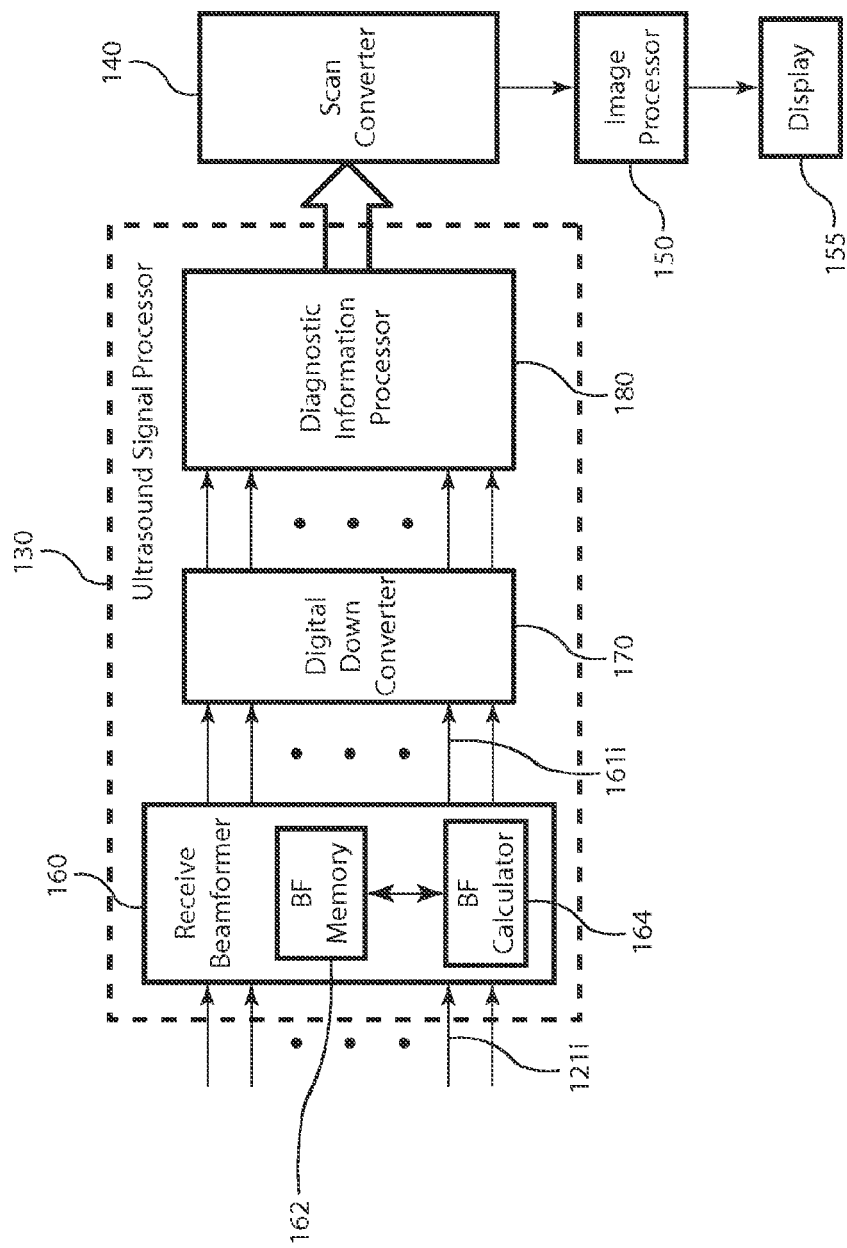
FIG. 2 is a block diagram of the ultrasound signal processor 130, in accordance with the prior art.

The ultrasound signal processor 130 performs the operations that extract the diagnostic information from the ultrasound signal samples, including beamforming, downconversion, B-mode processing and/or Doppler processing, described further with respect to FIG. 2. The ultrasound signal processor 130 can be implemented in one or more processors, such as a digital signal processor (DSP), field-programmable gate array (FPGA), microprocessor or CPU of a computer. The scan converter 140 performs coordinate transformations of a frame of processed samples to produce a frame of ultrasound image samples having a raster (rectilinear) format. The image processor 150 can apply additional image enhancement operations to the ultrasound image samples. The display 155 provides two-dimensional or three-dimensional images for analysis by a user.

FIG. 2 is a block diagram of the ultrasound signal processor 130, in accordance with the prior art. Medical ultrasound systems can perform digital beamforming operations on the RF ultrasound signal samples output from the ADC bank 120. The receive beamformer 160 applies delay, apodization (attenuation) and addition operations to the ultrasound signal samples to form a 1-D array of beamformed samples, or beam, corresponding to a particular direction in the field of view. The receive beamformer 160 produces a number of 1-D arrays of beamformed samples corresponding to a number of directions in the field of view. The receive beamformer 160 includes a beamformer (BF) memory 162 to store the ultrasound signal samples for the delay and addition operations of the beamform (BF) calculator 164. The BF calculator 164 can form multiple beams using the ultrasound signal samples retrieved from the BF memory 162 for the same received pulse. The BF calculator 164 can apply interpolation between adjacent ultrasound signal samples to improve the phase resolution of the calculated beams. The receive beamformer 160 can also apply weighting functions to the samples prior to the addition operations to implement spatial windowing functions or apodization. The beamformed samples calculated for each angle are provided to a corresponding beamformer output channel 161i. The receive beamformer 160 typically has fewer output channels 161i than input channels, comprising the ADC output channels 121i. In this configuration, the beamformed samples have an RF center frequency. The digital down converter (DDC) 170 demodulates the beamformed samples to baseband to generate complex baseband I and Q samples for each beam. As an alternative or in addition to the DDC 170, a bandpass filter can be applied to the beamformed samples at a frequency band centered at the desired frequency or the DDC 170 can demodulate the beamformed samples to an intermediate frequency (IF) instead of baseband. Alternative architectures in the art include analog beamforming before analog to digital conversion and digital downconversion of ultrasound signal samples prior to beamforming.

The diagnostic information processor 180 performs the appropriate operations on the I,Q samples for the desired type of ultrasound image. B-mode processing generates information representing the intensity of the echo signal. The magnitudes of the I,Q samples can be calculated to form the detected samples for B-mode imaging. Doppler processing estimates the velocity, variance of velocity and energy from the I,Q samples to form Doppler detected samples. The spatial coordinates of the B-mode detected samples and the Doppler-detected samples correspond to the geometry of the beamformed samples. The scan converter 140 performs coordinate transformations of the detected samples to produce frames of data having raster format appropriate for display. The image processor 150 performs additional image processing of the frames of samples prior to display as two-dimensional or three-dimensional images.

Figure 3:
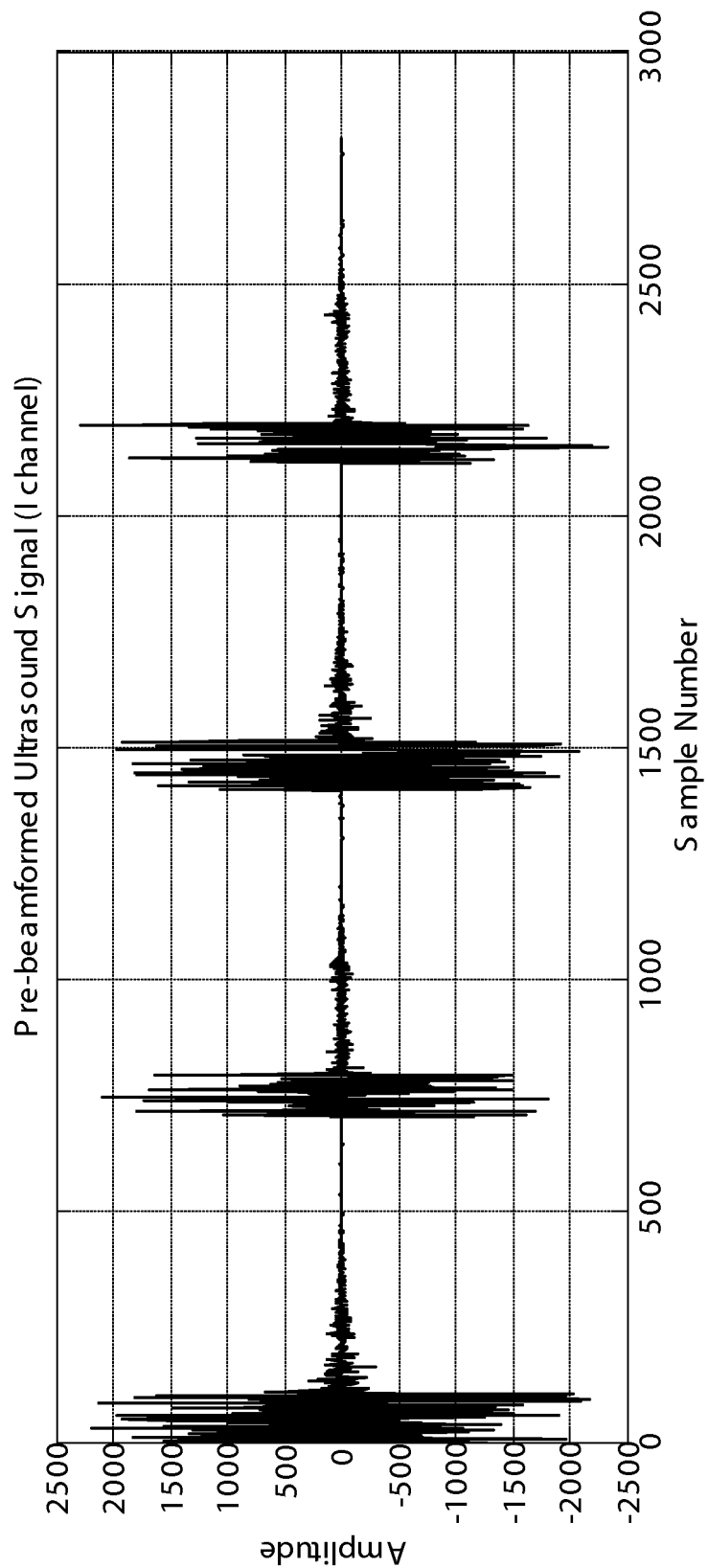
FIG. 3 is a plot of ultrasound signal samples prior to beamforming, in accordance with the prior art.
Figure 4:
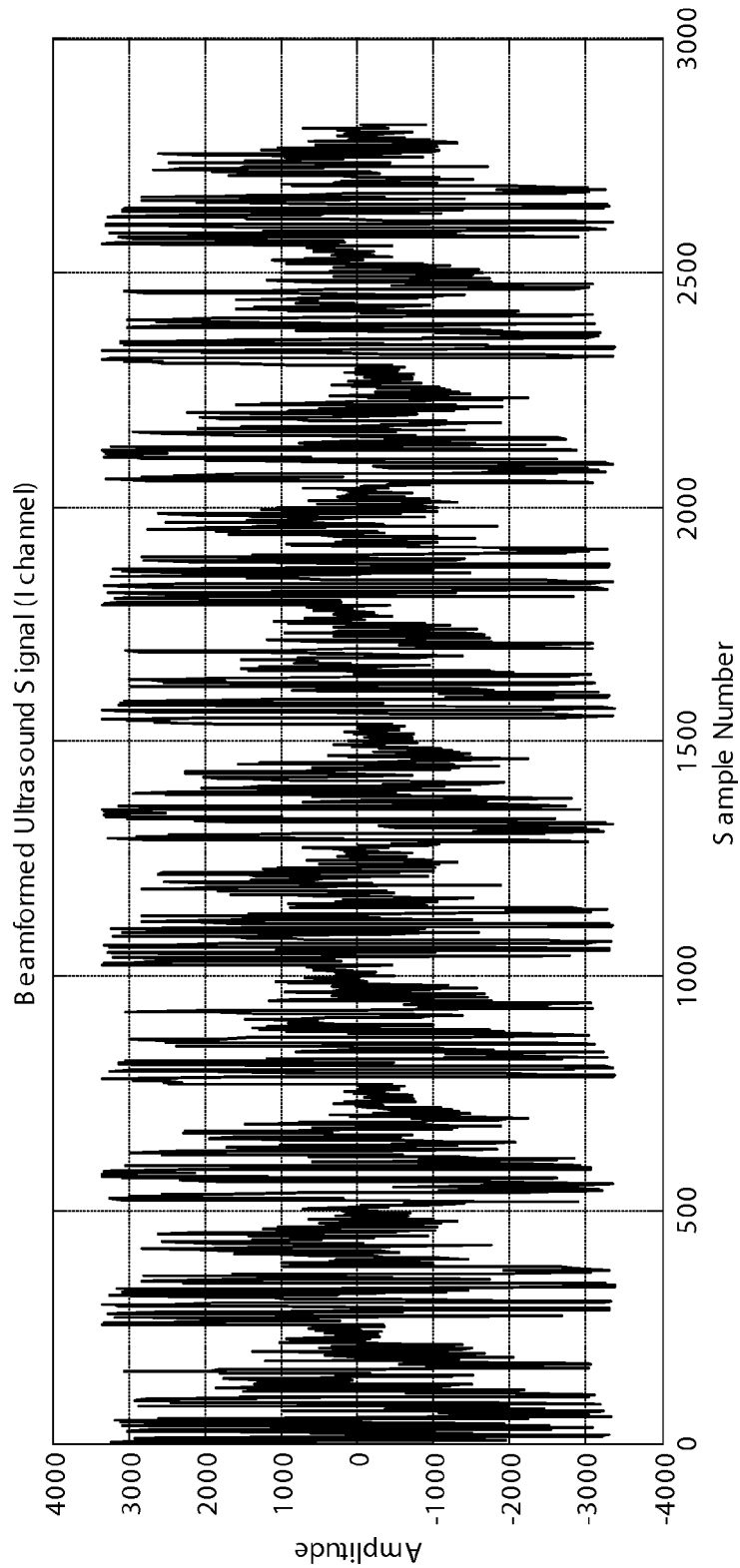
FIG. 4 is a plot of the in-phase samples of a beamformed ultrasound signal corresponding to one beamformer output channel, in accordance with the prior art.

FIG. 3 is a plot of ultrasound signal samples prior to beamforming. The plot displays the in-phase samples for four pulse echoes sampled by one ADC of an array of ADCs. For this example, digital down conversion has been applied to the ultrasound signal samples output from the ADC, prior to beamforming, to form the I,Q samples. FIG. 4 is a plot of the in-phase samples of a beamformed ultrasound signal corresponding to one beamformer output channel. For this example, the beamformer combines multiple sequences of I,Q samples output from multiple ADCs by applying delays and weighting functions to the I,Q samples.

Figure 5:
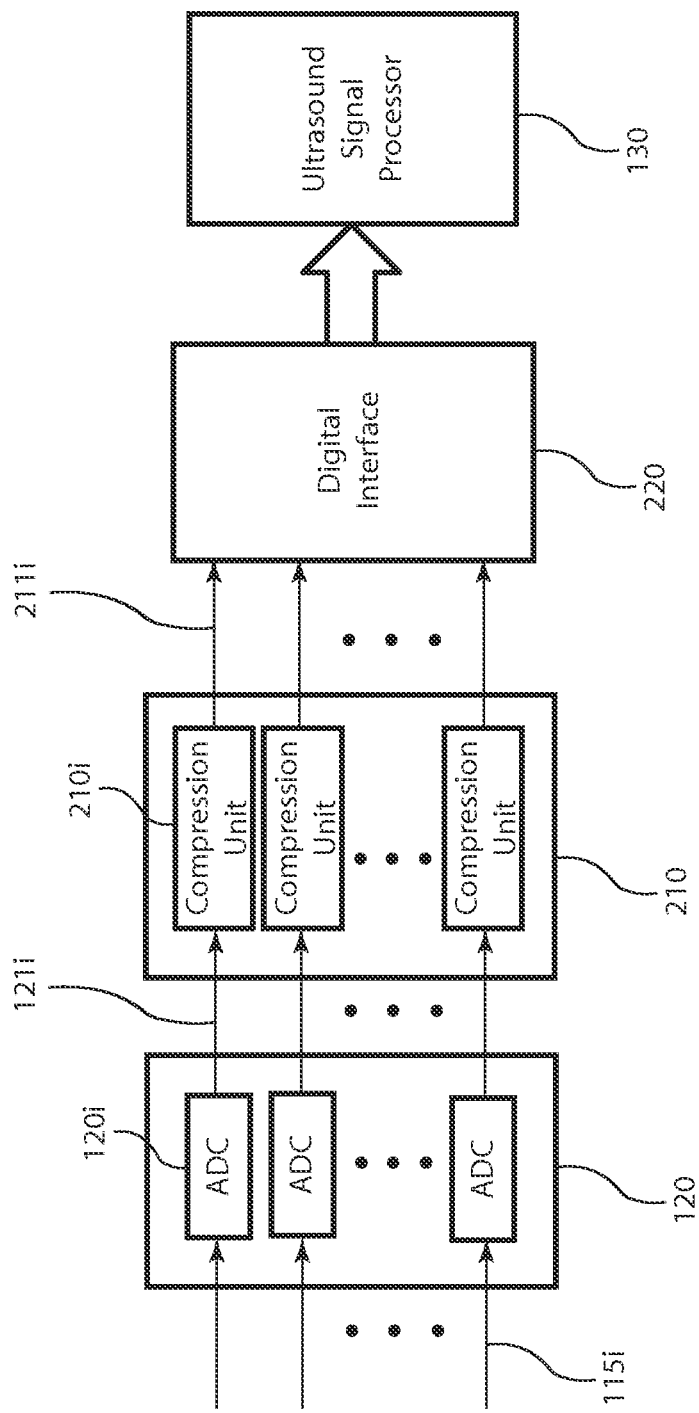
FIG. 5 is a block diagram of an ultrasound system that includes compressing signal samples output from the bank of ADCs, in accordance with a preferred embodiment.

FIG. 5 is a block diagram of an ultrasound system that includes compressing ultrasound signal samples output from the bank of ADCs 120, in accordance with a preferred embodiment. The compressor 210 includes a plurality of compression units 210i. The plurality of compression units 210i compresses the plurality of sequences of signal samples representing analog ultrasound signals output from respective transducer elements (e.g. 110i of FIG. 1) to form a plurality of sequences of compressed samples at the compressor output 211i. The compression unit 210i receives the sequence of signal samples from the ADC output 121i of the corresponding ADC 120i representing the analog ultrasound signal output from the corresponding transducer element 110i during a sampling window, where a sampling window is an interval of time during which the analog ultrasound signal represents the echoes reflected from a corresponding depth range in the subject. The compression unit 210i applies compression operations to the particular sequence of signal samples at its input independently of the signal samples representing analog ultrasound signals output from other transducer elements during the same sampling window to produce a corresponding sequence of compressed samples at the compressor output 211$i$. Alternatively, a compression unit 210$i$ may compress samples from more than one ADC where signal samples from a particular ADC 120$i$ are compressed independently from signal samples representing analog ultrasound signals output from other transducer elements during the same sampling window. The present description assumes that each ADC 120$i$ produces a sequence of real-valued samples. Alternatively, if the ADCs 120$i$ perform quadrature sampling to generate sequences of I and Q samples at each ADC output 121$i$, each sequence of I,Q samples is compressed independently. Compression is applied to the ultrasound signal samples prior to beamforming. The compressed samples are transferred across a digital interface 220 to the ultrasound signal processor 130 where they are decompressed for ultrasound processing operations. The data transfer bandwidth required for the digital interface 220 for transfer of the compressed samples is reduced compared to the bandwidth for transferring the streams of uncompressed ultrasound signal samples.

Figure 6:
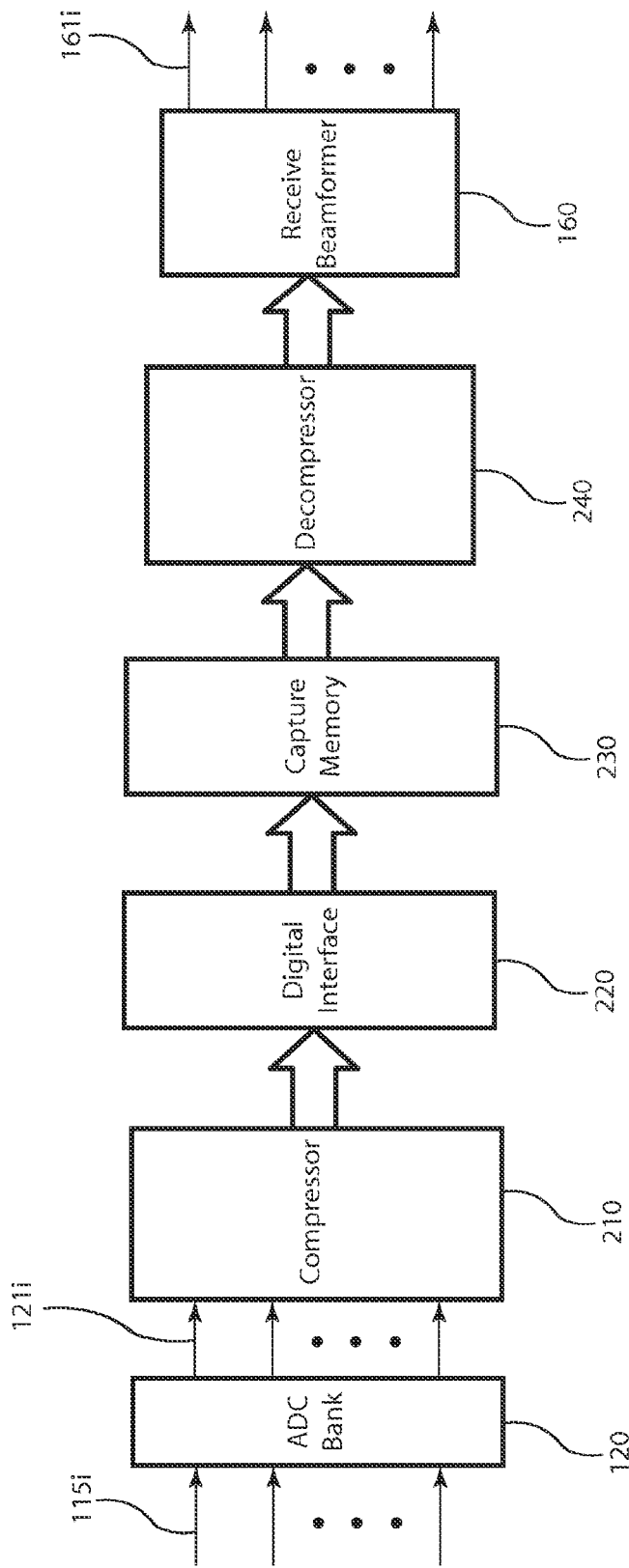
FIG. 6 is a block diagram of an ultrasound system that includes compressing the ultrasound signal samples and storing the compressed samples in a capture memory, in accordance with an alternative configuration.

FIG. 6 is a block diagram of an ultrasound system that includes compressing the ultrasound signal samples and storing the compressed samples in a capture memory, in accordance with an alternative configuration. After transfer across the digital interface 220, the compressed samples are stored in a capture memory 230. The capacity of the capture memory 230 sufficient for storing the compressed samples is reduced, thus conserving system resources. The decompressor 240 decompresses the compressed samples retrieved from the capture memory. The receive beamformer 160 applies beamforming operations to the decompressed samples to form a sequence of beamformed samples at each beamformer output channel 161$i$. As described with respect to FIG. 2, digital downconversion and/or filtering can be applied to the decompressed samples prior to the beamforming operations.

Figure 7:
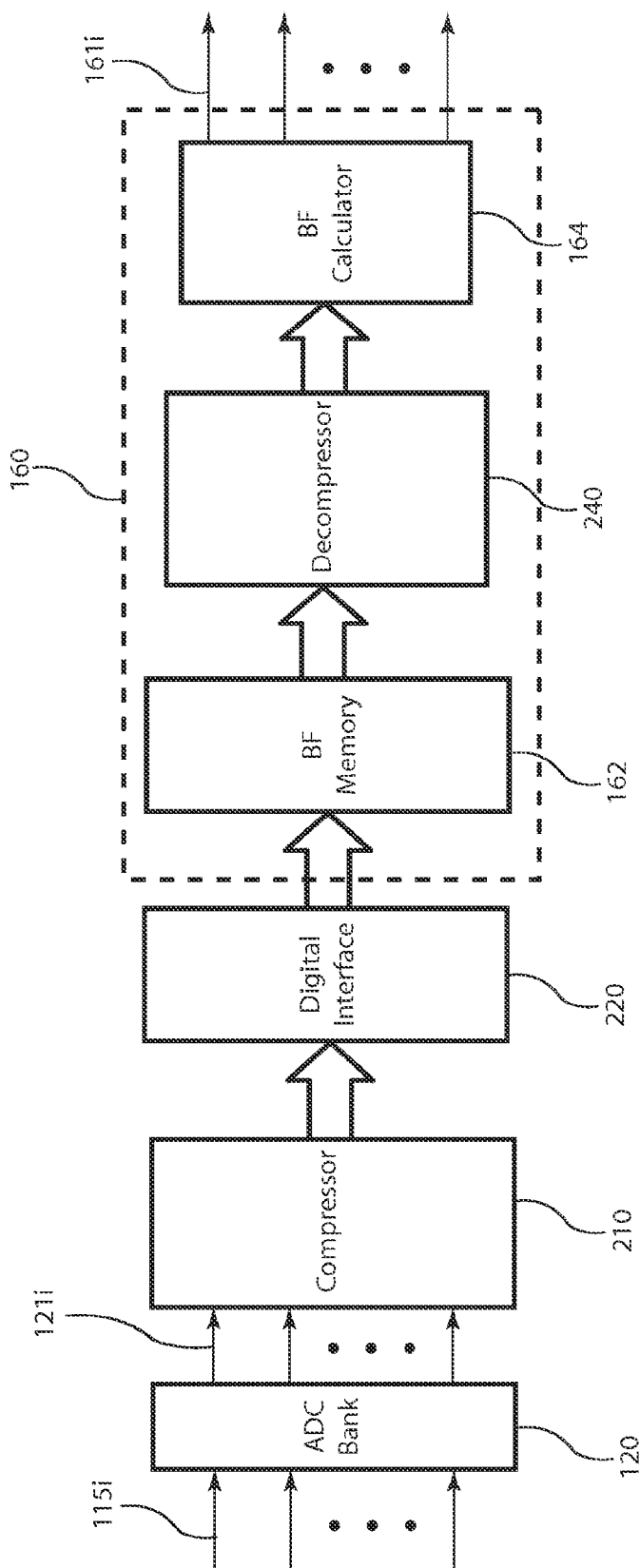
FIG. 7 is a block diagram of an ultrasound system where the compressed samples are stored in a beamformer memory, in accordance with an alternative configuration.

FIG. 7 is a block diagram of an ultrasound system where the compressed samples are stored in a beamformer memory, in accordance with an alternative configuration. The receive beamformer 160 stores the compressed samples in the beamformer (BF) memory 162 and retrieves the compressed samples when needed for beamforming operations. The decompressor 240 processes the compressed samples retrieved from the BF memory and provides the decompressed samples to the BF calculator 164. The BF calculator 164 applies the beamforming operations to the decompressed samples. The BF calculator 164 can also perform the additional operations on the decompressed samples for spatial filtering, etc., described with respect to FIG. 2.

Figure 8:
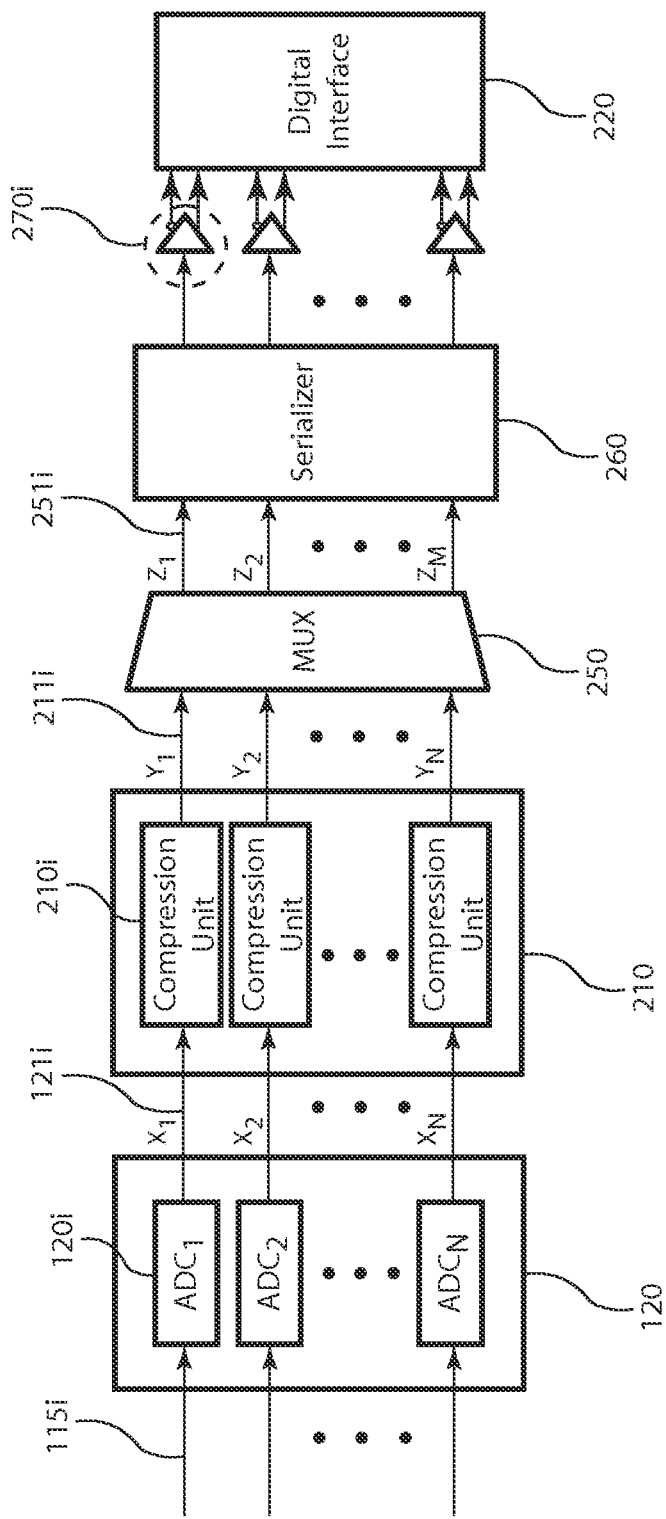
FIG. 8 is a block diagram for an ultrasound system including multiplexing the compressed samples for transfer across fewer data ports.

Since the compressed samples have fewer bits per sample than the original ultrasound signal samples, the compressed samples can be transferred across the digital interface 220 using fewer data ports than the uncompressed samples. FIG. 8 is a block diagram for an ultrasound system including multiplexing the compressed samples for transfer across fewer data ports. For this example, the ADC bank 120 includes N ADCs 120$i$, ADC 1 to ADCN, producing streams of signal samples at the N ADC output channels 120$i$, $X_1$ to $X_N$. The compression units 210$i$ produce corresponding streams of compressed samples at N compressor outputs 211$i$, $Y_1$ to $Y_N$. The compressed samples having a reduced bit rate are provided to the data ports 270$i$. Preferably, the data ports 270$i$ provide low voltage differential signaling (LVDS) data transmission. Alternatively, the data ports 270$i$ can use serializer-deserializer (SerDes) interfaces for data transmission. The document entitled "LVDS Owner's Manual Including High-Speed CML and Signal Conditioning", Fourth Edition, published in Jan. 2008 by National Semiconductor describes LVDS devices and architectures. The LVDS data transmission has desirable characteristics, including a maximum data transfer rate of 3.125 Gbps, low noise and low power consumption. The differential signaling requires two I/O pins per channel output, one for the positive differential output and one for the negative differential output, referred to as an LVDS pair. The data port 270$i$ has excess bandwidth when the bit rate of the compressed samples at compressor output $Y_i$ is lower than the port's maximum data transfer rate. The excess bandwidth can be utilized by combining multiple streams of compressed samples for transfer over a given data port 270$i$. The multiplexer 250 combines N sequences of compressed samples to form M sequences of multiplexed compressed samples, where M<N, for transfer over M data ports 270$i$. The number of compressed sample streams that can be combined is limited by the bandwidth of the data transfer port 270$i$. For example, for N=16 ADCs, where each ADC produces ultrasound signal samples with 12 bits per sample at a sample rate of 50 megasamples per sec. (Msps), the bit rate at each ADC output channel 121$i$ is 600 Mbps. Suppose the data port 270$i$ has a data transfer rate of up to 800 Mbps and the compressor 210 produces a compression ratio of 3:1. The compressed sample sequence $Y_i$ at compressor output 121$i$ has a bit rate of 200 Mbps. In this case, one data port 270$i$ has sufficient bandwidth to transfer compressed samples from four compressor outputs at the data transfer rate of 800 Mbps. For this example, the multiplexer 250 combines the compressed samples from a group of four compressed sequences, $Y_i$, $Y_{i+1}$, $Y_{i+2}$ and $Y_{i+3}$, to form a corresponding sequence of multiplexed compressed samples $Z_j$ at one multiplexer output 251$i$. In this example, the number of sequences of multiplexed compressed samples and corresponding active data ports is M=N/4=4. The serializer 260 provides sequences of bits to the corresponding data ports 270$i$.

The advantages of multiplexing the compressed samples to use M data ports include using fewer physical data ports, which in turn reduces the connections and power consumption of the data ports. In applications where the bit rate of the compressed samples is fixed, the multiplexer 250 has a fixed number of multiplexer outputs 251$i$ for a fixed number of physical data ports 270$i$. Alternatively, a flexible architecture can support a variable number active data ports depending on the bit rate of the compressed samples. For the flexible architecture, the compressor 210 provides compressed samples at various bit rates that depend on a user selectable compression ratio parameter. A compression controller (not shown in FIG. 8) provides compression control parameters to the compression units 210$i$ so that the operations produce compressed samples with a bit rate that corresponds to the desired compression ratio. The compression controller provides multiplexing control parameters to the multiplexer 250 to indicate the number of sequences of multiplexed compressed samples to produce at the multiplexer outputs 251$i$. The compression controller can also respond to the user input to power down the inactive data ports, thus further conserving power.

It is also possible for the data ports 270$i$ to have excess bandwidth for certain values of the sample rate and bits per sample, even without compressing the signal samples. The data ports 270$i$ have excess bandwidth when the product of the sample rate and number of bits per sample results in a bit rate at the ADC output 121$i$ that is lower than the maximum data transfer rate of the data port 270$i$. For example, suppose the ADC clock frequency is 50 megahertz (MHz), corresponding to 50 Msps, and the sample width is 12 bits per sample so that each ADC 120$i$ produces 600 megabits per second (Mbps). The data transfer rate will be 600 Mbps for each data port 270*i*. For an LVDS port having a maximum data transfer rate of 800 Mbps, there is an unused bandwidth of 200 Mbps for each port. The data ports 270*i* will consume the same amount of power to transfer data at 600 Mbps as they would for transferring data at full capacity of 800 Mbps because LVDS interfaces are constant-current (thus constant-power) links. Port concentration exploits the excess data transfer capacity by combining bits from multiple ADC outputs and transmitting the combined data at a faster rate over fewer ports. Each data port transmits the combined data at a rate that is greater than the ADC bit rate and up to the maximum data transfer rate of each data port 270*i*.

Figure 9:
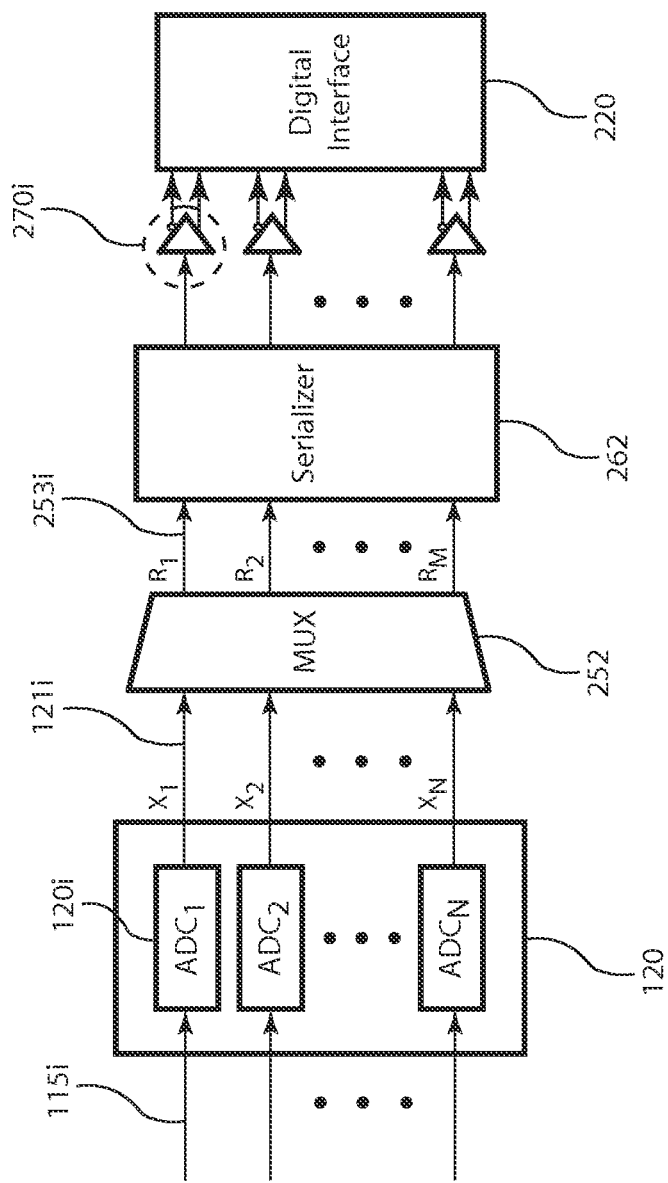
FIG. 9 is a block diagram of an ultrasound system that applies port concentration to the ADC outputs.

FIG. 9 is a block diagram of an ultrasound system that applies port concentration to the ADC outputs 121*i*. The N sequences of ultrasound signal samples at the N ADC outputs $X_1$ to $X_N$ are input to the multiplexer 252. The multiplexer 252 combines the samples from groups of ADC outputs to form M channels of multiplexed signal samples $R_1$ to $R_M$, where M<N. Each channel $R_i$ has a bit rate that is greater than the ADC bit rate at the ADC output 121*i*, but less than or equal to the maximum data transfer rate, in bits per second, of the data port 270*i*. The multiplexer 252 combines the samples by mapping the bits of N signal samples for each sample period to M subsets of bits. The serializer 262 serializes each of the subsets of bits for transfer by the corresponding data port 270*i*. Consider the above example where, in addition, the number N of ADCs is sixteen. The signal samples output from the sixteen ADCs 120*i* at an ADC bit rate of 600 Mbps can be combined into twelve bit streams, each with a bit rate of 800 Mbps. Twelve active data ports 270*i* would transfer the twelve bit streams, each at the data transfer rate of 800 Mbps (800 Mbps×12=600 Mbps×16). Depending on the sample rate, the number of bits per sample and the maximum data transfer rate, several configurations are possible.

Figure 10A:
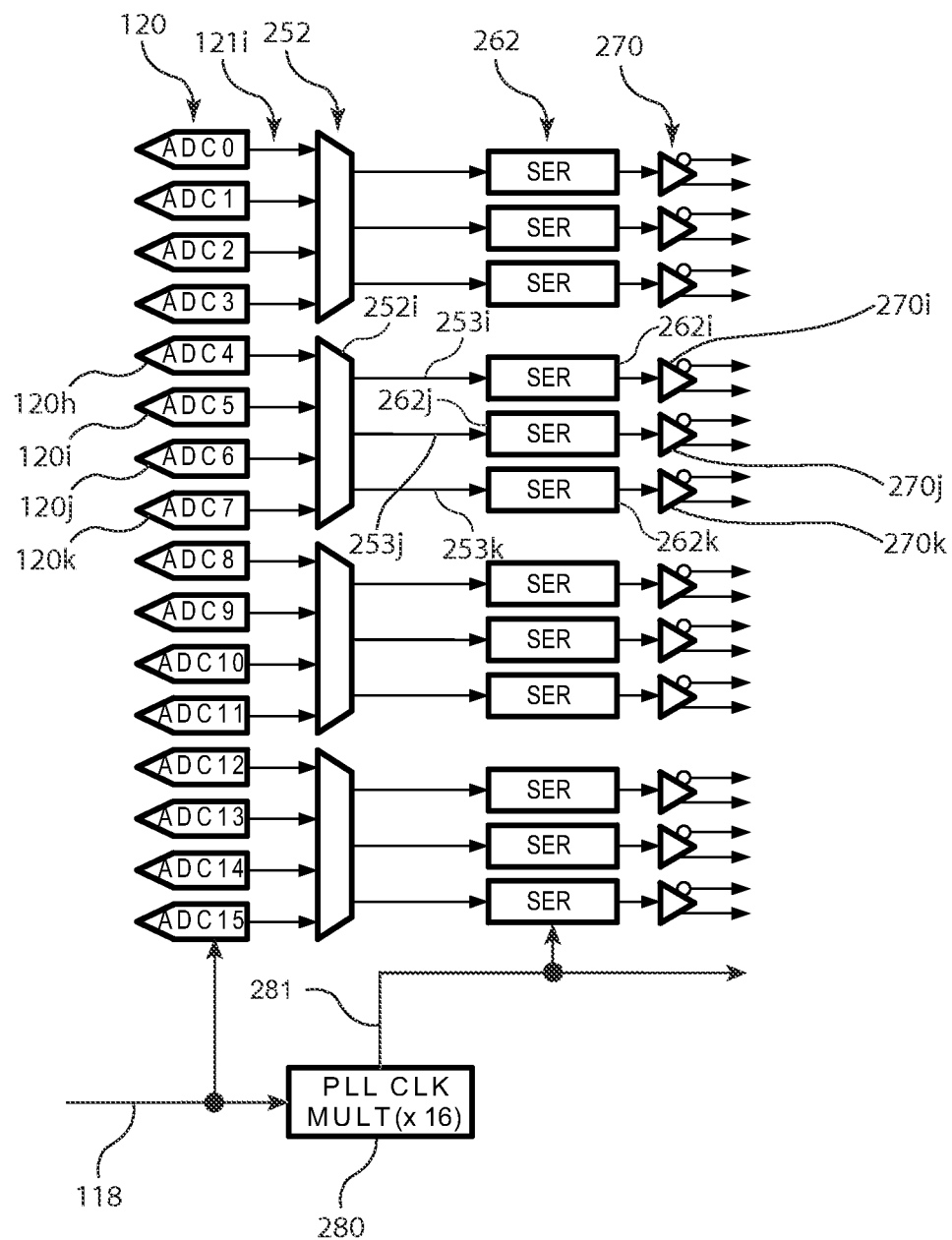
FIG. 10A is a block diagram of a port concentration configuration that includes twelve data ports for transferring data from sixteen ADCs.

FIG. 10A is a block diagram of a port concentration configuration that includes twelve data ports for transferring data from sixteen ADCs. This configuration can accommodate sample rates up to 50 Msps corresponding to ADC clock frequencies up to 50 MHz. The ADC input clock 118 carries a clock signal whose frequency corresponds to the ADC sample rate. The ADCs 120 respond to the ADC input clock 118 to sample the input analog signals at the sample rate. The multiplexers 252 receive the signal samples output from the bank of ADCs 120. Four ADCs 120*h*, 120*i*, 120*j* and 120*k* provide signal samples to one multiplexer 252*i*. The multiplexer 252*i* includes three outputs 253*i*, 253*j* and 253*k*. The multiplexer 252*i* reorders the 48 bits of the samples it receives during each sample period and distributes the reordered bits to three serializers 262*i*, 262*j* and 262*k*. Each serializer 262*i*, 262*j* and 262*k* receives a subset of the 48 reordered bits, in this case 16 bits, and serializes them for transfer by a corresponding port 270*i*, 270*j* and 270*k*. The phase lock loop (PLL) 280 produces the data clock 281 having a frequency that is 16 times the ADC clock frequency. The PLL 280 operates on the ADC input clock to produce the data clock 281 for the serializers 262 and the data ports 270. The data clock frequency corresponds to the data transfer rate of the bits output from each serializer 262*i*. The data clock frequency is the ADC clock frequency multiplied by the number of multiplexed bits per sample period, in this case sixteen. The twelve data ports 270 transfer the serialized bits at a data transfer rate that is 16 times the sample rate.

Figure 10B:
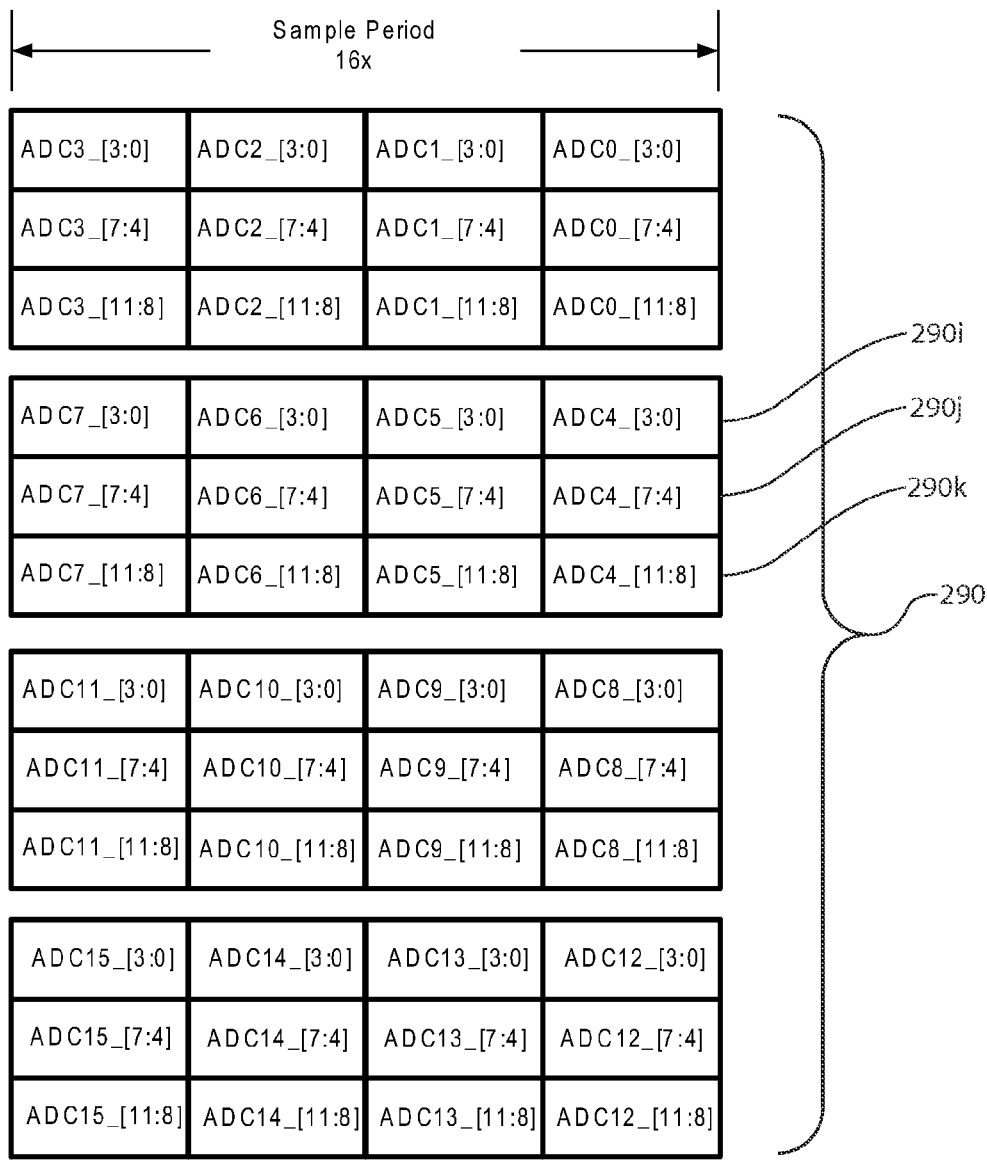
FIG. 10B illustrates the arrangement of bits provided to the data ports 270 during one sample period for the configuration of FIG. 10A.

FIG. 10B illustrates the arrangement of bits provided to the data ports 270 during one sample period for the configuration of FIG. 10A. Table 290 depicts the bit mapping of the sample bits output from the sixteen ADCs during one sample period. For the configuration having four multiplexers 252 and three serializers 262, the multiplexers 252 group the bits of each signal sample into blocks of 4 bits. The multiplexer 252*i* directs the first block of bits to the serializer 262*i*, the second block of bits to the serializer 262*j* and the third block of bits to the serializer 262*k*. Lines 290*i*, 290*j* and 290*k* represent the bit mapping for serializers 262*i*, 262*j* and 262*k*, respectively. Other bit mappings resulting in different bit orders can be used, provided that each of the serializers 262 outputs sixteen mapped bits during one sample period. After transfer across the digital interface 220, the received multiplexed bits are reordered in accordance with the inverse bit mapping to restore the original sequences of signal samples.

Figure 11:
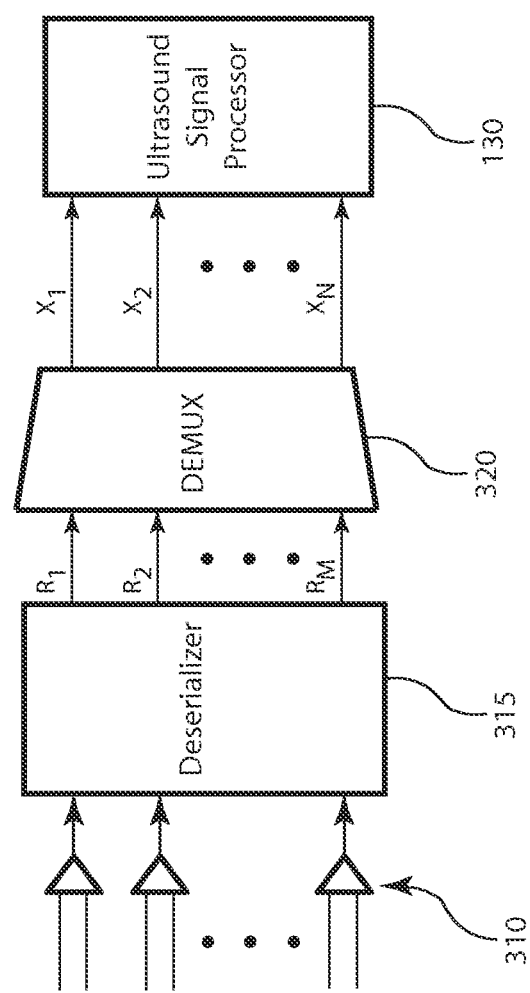
FIG. 11 is a block diagram of reordering the received multiplexed bit streams resulting from port concentration to restore the original sequences of signal samples.

FIG. 11 is a block diagram of reordering the received multiplexed bit streams resulting from port concentration to restore the original sequences of signal samples. In the port concentration mode, the receiver requires fewer input data ports 310, resulting in power savings and reduced complexity. The input data ports 310 are LVDS receivers. Each LVDS receiver receives the differential signal produced by LVDS transmission and generates a logic state that reproduces the corresponding received bits. The deserializer 315 converts the received serial bits to M parallel channels of multiplexed signal samples $R_1$ to $R_M$. The demultiplexer 320 rearranges the bits of the multiplexed signal samples to the order of the original sequences $X_1$ to $X_N$ of signal samples. The ultrasound signal processor 130 then applies operations, such as beamforming or digital downconversion, to the reproduced sequences of signal samples. Additional alternatives for the port concentration mode are described in the '988 application.

The compression methods applied by compression units 210*i* include block floating point encoding and computing first or higher order derivatives of the signal samples followed by block floating point encoding. Huffman or other types of encoding can be alternatives to block floating point encoding.

The preferred embodiment of the compression unit 210*i* applies block floating point encoding to groups of consecutive signal samples from the ADC output 121*i*, each group having N_GROUP samples. The maximum exponent for the N_GROUP samples is encoded and the N_GROUP samples are encoded according to the following steps.

For the first group of N_GROUP samples:
1) Determine the exponent (base 2) for the sample with the maximum magnitude, such as by calculating the $\log_2$ of the maximum magnitude in each group of N_GROUP samples. This indicates the number of bits per encoded sample, or n_exp(0).
2) Absolute encode the exponent n_exp(0) of the first group using S bits, where S is the original number of bits per sample.
3) Encode the N_GROUP samples using n_exp(0) bits per sample.

For the $i^{th}$ group of N_GROUP samples (i>0):
4) Determine the $i^{th}$ exponent (base 2) for the sample with the maximum magnitude, which indicates the number of bits per encoded sample in the $i^{th}$ group, or n_exp(i);
5) Differentially encode the $i^{th}$ exponent by subtracting n_exp(i) from n_exp (i−1) to determine an $i^{th}$ difference value. Encode the $i^{th}$ difference value using a corresponding token, where shorter tokens represent more common difference values and longer tokens represent less common difference values.
6) Encode the $i^{th}$ group of N_GROUP samples using n_exp (i) bits per sample.

For the first group of samples, the exponent n_exp(0) is directly encoded. For example, the exponent n_exp(0) can be encoded as follows, where S is the original number of bits per sample:

| | |
|---|---|
| a. 0: | n_exp(0) = 0 (all 4 sample values are zero) |
| b. 1: | n_exp(0) = 2 (2 bits per sample) |
| c. 2: | n_exp(0) = 3 (3 bits per sample) |
| d. etc. until S − 1: | n_exp(0) = S (S bits per sample) |

For the $i^{th}$ group, the exponent n_exp(i) is differentially encoded using a prefix code, where no codeword is the prefix of another codeword. The preferred differential encoding is as follows:
1. Calculate difference: e_diff=n_exp(i)−n_exp(i−1)
2. Encode e_diff as follows:

| | |
|---|---|
| a. 0: | e_diff = e(i) − e(i − 1) |
| b. 101: | e_diff = +1 |
| c. 110: | e_diff = −1 |
| d. 1001: | e_diff = +2 |
| e. 1110: | e_diff = −2 |
| f. Etc. | |

Alternatively, the exponents n_exp(i) may be Huffman encoded instead of differentially encoded.

Figure 12:
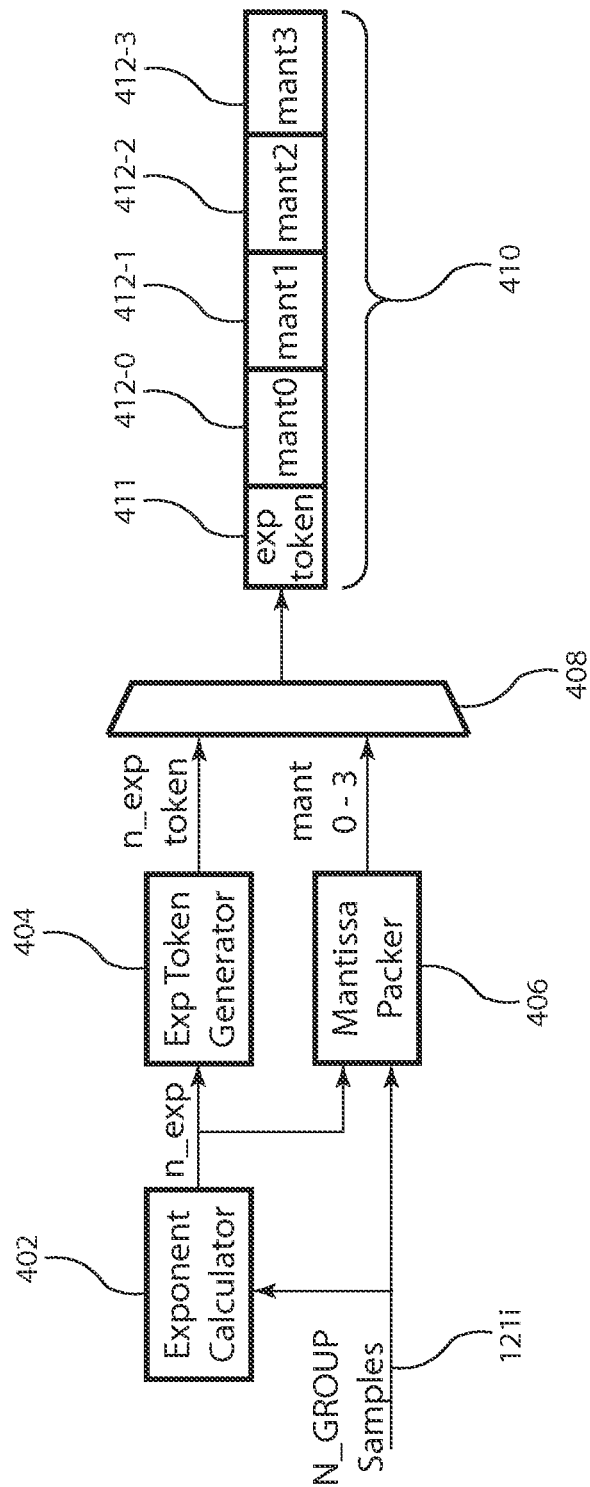
FIG. 12 is a block diagram of the block floating point encoder where N_GROUP=4.
Figure 13:
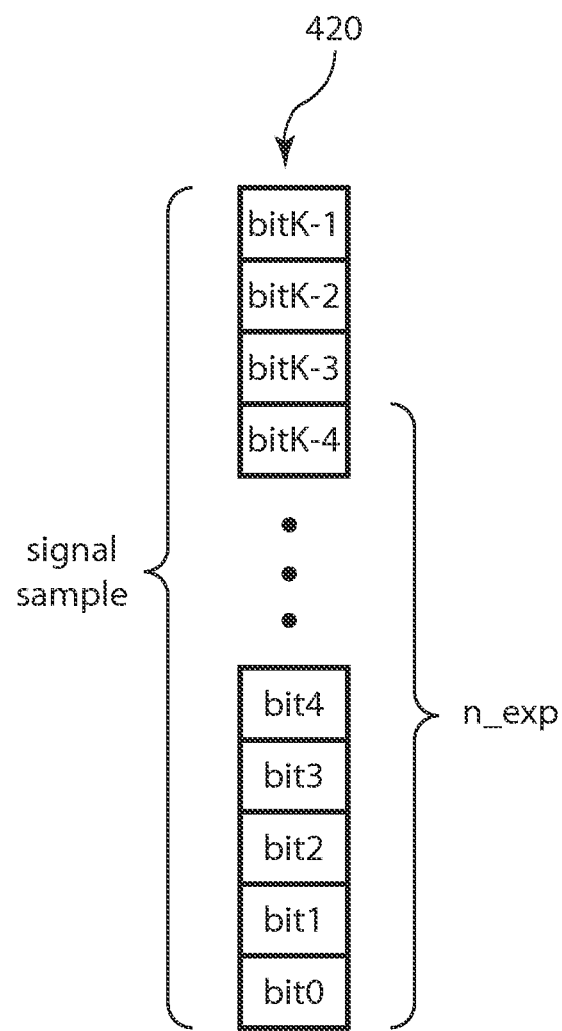
FIG. 13 illustrates an example of selecting n_bits of a signal sample for encoding.

FIG. 12 is a block diagram of the block floating point encoder where N_GROUP=4. The exponent calculator 402 determines the maximum exponent in bits, n_exp, for the N_GROUP samples as in step 1 and step 4. The exponent token generator 404 encodes the n_exp values as in step 2 and step 5. The mantissa packer 406 encodes the mantissas for the N_GROUP samples as in step 3 and step 6. FIG. 13 illustrates an example of selecting n_bits of a signal sample for encoding. The input signal sample 420 is represented by K bits. The n_exp lower bits of the sample 420 are selected for encoding. The sign bit for the sample is appended to the selected bits and the resulting sequence of bits represents the mantissa. Returning to FIG. 12, the multiplexer 408 packs the encoded exponent token 411 followed by the N_GROUP mantissas to form the compressed group 410 representing the N_GROUP compressed samples. For this example, the compressed group 410 includes the exponent token 411 followed by the sequence of four packed mantissas 412-0, 412-1, 412-2 and 412-3. The compression unit 210*i* concatenates consecutive compressed groups to form the data portion of a compressed packet at the compressor output 211*i*. The preferred sizes for N_GROUP are three or four samples per group. However, variable group sizes may also be used.

Encoding the mantissas and exponents separately can provide additional compression and mitigate compression error. The difference values of consecutive exponents are calculated and encoded. The exponents vary slowly, so there are relatively few nonzero values separated by strings of zero values. The exponent difference values can be efficiently encoded by representing only the nonzero difference values and their corresponding positions. The position can be represented by the corresponding index value or relative to the position of the last nonzero difference value. Encoding of the exponent difference values is lossless, which prevents relatively large errors. For decoding the exponents, the exponent values are reconstructed by integrating the exponent difference values and decoding the corresponding position locations. For decoding of the mantissas, each reconstructed mantissa value is restricted to so that it does not change the value of the corresponding exponent of the decoded sample. For a decoded exponent of n_exp, the reconstructed mantissa can have a maximum value of $2^{n\_exp}-1$. This prevents compression error in the mantissa from changing the value of the exponent.

Figure 14:
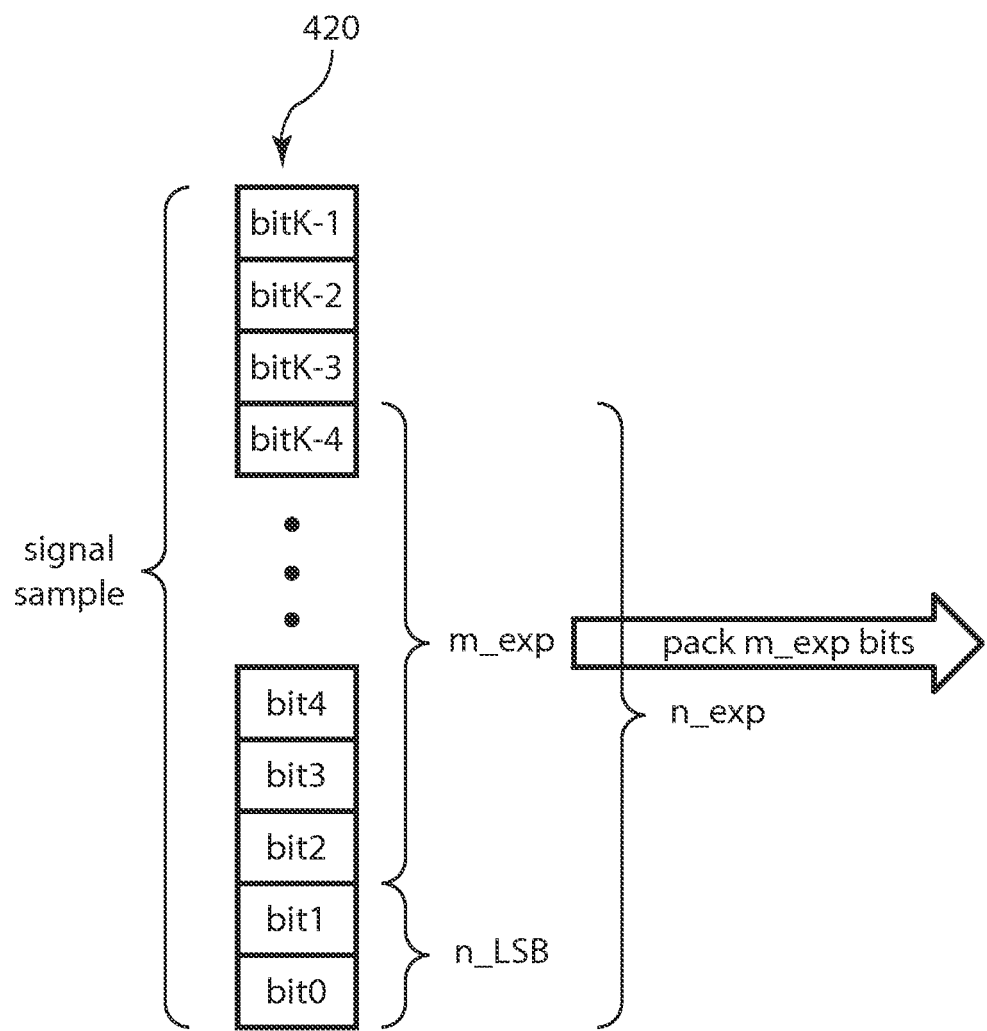
FIG. 14 illustrates an example of selecting bits for representing the reduced mantissa.
Figure 16:
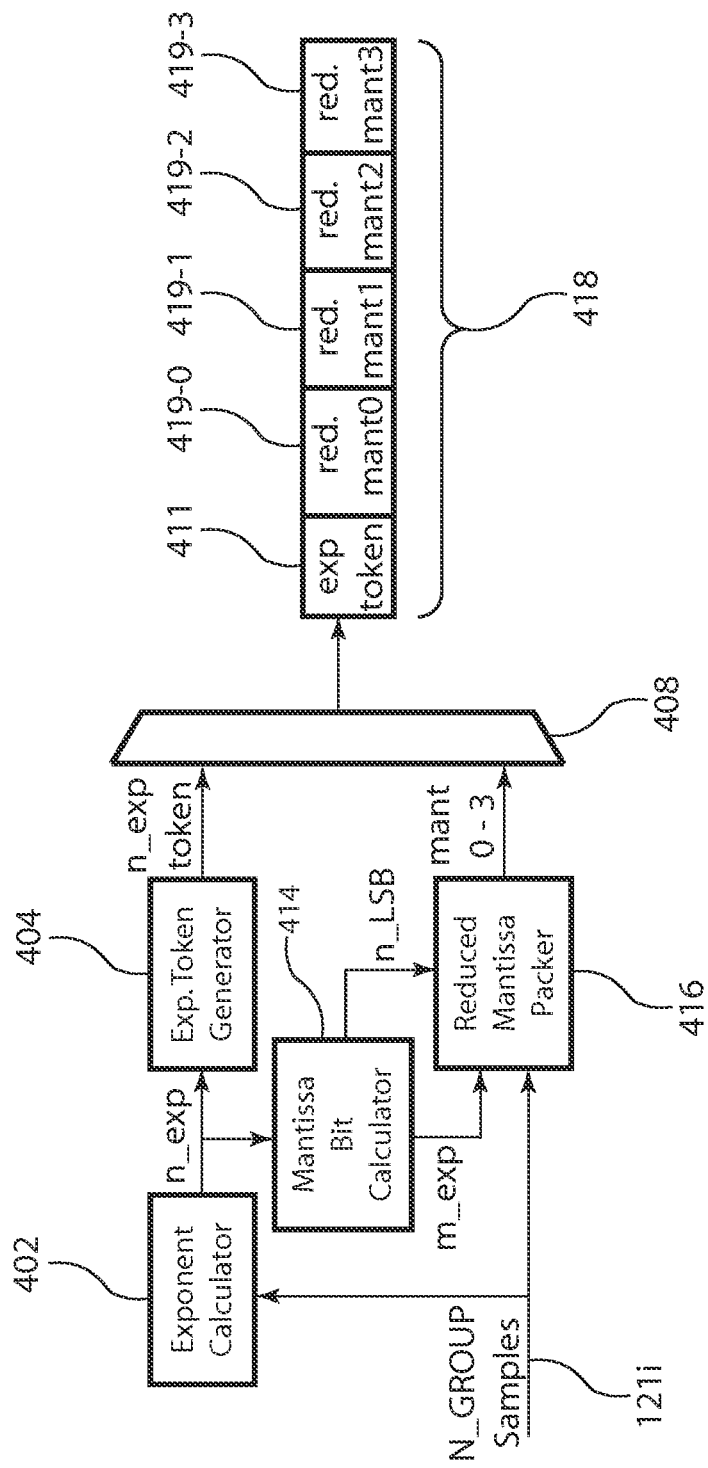
FIG. 16 is a block diagram of block floating point encoding using reduced mantissas.

An alternative block floating point encoding method includes reducing the number of bits representing the mantissa and differential encoding of the exponents as described above. The number of bits representing the mantissas of the N_GROUP samples is reduced by selectively removing a number of least significant bits (LSBs) from each mantissa, depending on the value of n_exp for the group. FIG. 14 illustrates an example of selecting bits for representing the reduced mantissa. The n_exp is determined as in step 1 and step 4 above. Instead of encoding all of the n_exp lower bits of the mantissa, a number n_LSB of bits, starting with the least significant bit, are removed. The remaining m_exp bits (m_exp=n_exp−n_LSB) are selected for encoding. The value of n_LSB depends on the value of n_exp according to a formula or a table. FIG. 15 is a table of exemplary values of n_exp, n_LSB and m_exp. For larger values of n_exp, more LSBs are removed by truncating or rounding to form the reduced mantissa having m_exp bits. For example, if n_exp is 12, 3 LSBs are removed so that 9 mantissa bits are retained for packing the N_GROUP reduced mantissas. The compressor 210 can store a lookup table of values of n_exp, n_LSB and m_exp. Alternatively, the compressor 210 can represent n_LSB and m_exp as a function of n_exp and calculate their values when needed. FIG. 16 is a block diagram of block floating point encoding using reduced mantissas. For the each group of N_GROUP samples, the exponent calculator 402 determines the maximum exponent n_exp as described above. The mantissa bit calculator 414 determines the number of bits m_exp in the reduced mantissa using a lookup table or formula. The reduced mantissa packer 416 selects the m_exp bits for each of the N_GROUP samples. The multiplexer 408 then packs the exponent token 411 followed by the reduced mantissas 419-0, 419-1, 419-2 and 419-3 to form the compressed group 418. For some conditions, no LSBs are removed from the group of N_GROUP samples. For example, when the magnitude of one or more samples in the N_GROUP samples is less than an acceptable minimum, the N_GROUP mantissas including the original LSBs will be packed. The sequence of compressed samples can include compressed groups with or without reduced mantissas.

A compression controller provides compression control parameters to the compression units 210*i* for block floating point encoding. There can be multiple alternative lookup tables or formulas for n_LSB, m_exp and n_exp. The compression control parameters include N_GROUP and selection parameters for alternative lookup tables or formulas for n_LSB, m_exp and n_exp. The compression control parameters can be uniform for all the compression units 210*i*. Alternatively, the compression control parameters can have different values for the different compression units 210*i*. The compression controller can respond to user input to select the compression control parameters.

The compressed samples may be inserted into the data portions of compressed packets for transfer over the digital interface 220. The sequence of compressed samples corresponding to a received pulse digitized by an ADC 120*i* may be arranged in one or more compressed packets. Alternatively, sequences of compressed samples from multiple ADCs 120*i* may be combined to form a compressed packet for transfer over a given data port 270*i*, as described with respect to FIG. 8. The header portion of the compressed packet contains identifying information for the packet. The header can also contain control data that represent the compression control parameters for the compressed samples in the packet. The information on the compression control parameters can be used by the decompressor 240 to configure the decompression operations.

For decompression, the decompressor 240 applies block floating point decoding to the sequences of compressed samples. For each group of N_GROUP compressed samples, the decompressor 240 decodes the exponent token to determine the value of n_exp. The differentially encoded exponents are integrated to form the value of n_exp. The N_GROUP mantissas are then reconstructed by unpacking the bits for each mantissa from the compressed group 410 or 418 and mapping the bits to the decompressed sample. The decompressed samples can be represented by the original number of bits per sample or a different number of bits per sample depending on the downstream processing requirements of the ultrasound signal processor 130. For the block floating point encoder using reduced mantissas, the decompressor 240 also includes a lookup table or formula for determining the values n_LSB based on the decoded values of n_exp. The unpacked bits for the reduced mantissa are appended by n_LSB bits, which can be zeros or dithered values, to approximate the original sample values.

The '533 patent describes algorithms for compression and decompression of certain bandlimited signals. Some of the alternative compression methods described below are modifications of the algorithms of the '533 patent for ultrasound signal samples.

Another alternative for compression of ultrasound signal samples is calculating differences followed by encoding. Calculating first or higher order differences of the ultrasound signal samples can result in difference samples having smaller magnitudes than the original signal samples. Encoding the difference samples can result in greater compression than encoding the samples themselves. Calculating the differences of consecutive samples of the ADC output 121$i$ can be followed by block floating point encoding of the difference samples, as described above. In this case, the difference samples are input to the block floating point encoder instead of the signal samples of the ADC output 121$i$. Alternatively, Huffman encoding or other encoding can be applied to the difference samples.

Figure 17:
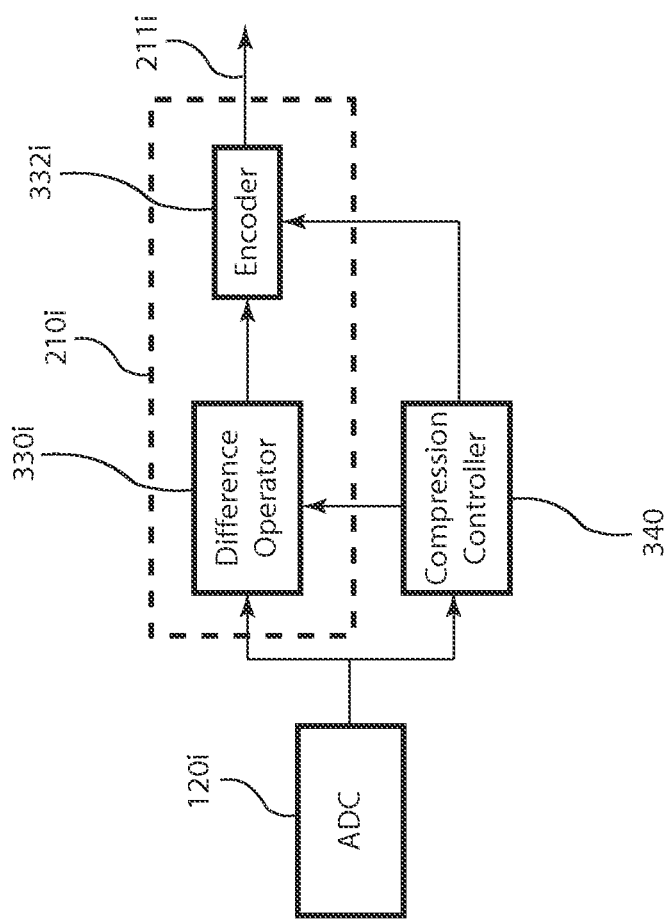
FIG. 17 shows a block diagram of the compression unit 210i that includes differencing operations.

FIG. 17 shows a block diagram of the compression unit 210$i$ that includes differencing operations. The compression unit 210$i$ receives ultrasound signal samples from the ADC 120$i$. The compression controller 340 provides compression control parameters for the difference operator 330$i$ and encoder 332$i$ of each compression unit 210$i$. The compression control parameters for the difference operator 330$i$ can select first, second or higher order differences. The difference operator 330$i$ applies the selected differencing order to produce the difference samples. The compression control parameter can also select bypassing the difference operations so that the encoder 332$i$ encodes signal samples instead of the difference samples. The compression control parameter for the encoder 332$i$ can indicate parameters for the block floating point encoder, as described above, or parameters for a Huffman encoder or another encoder. The compression control parameters can be the same or different for the different compression units 210$i$.

Figure 18:
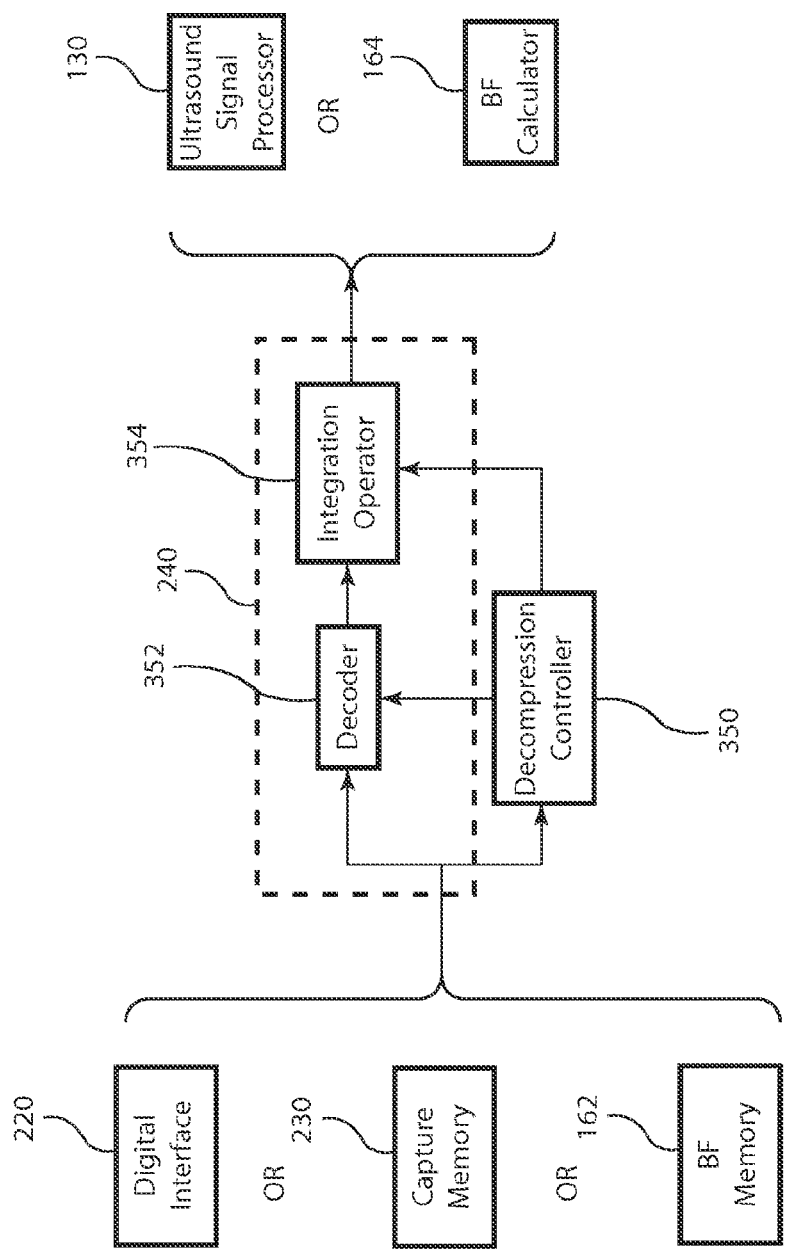
FIG. 18 is a block diagram of the decompressor.

FIG. 18 is a block diagram of the decompressor 240. The decompressor receives compressed samples from the digital interface 220, the capture memory 230 or the beamformer memory 162, depending on the system architecture. The decoder 352 inverts the operations of the encoder 332$i$ to form decoded samples. For example, the decoder 352 performs block floating point decoding, Huffman decoding or other decoding. The integration operator 354 adds the decoded difference samples to invert the first or higher order differencing performed for compression. If differencing was not performed for compression, the integration operator 354 would be bypassed. The decompression controller 350 provides control parameters to the decoder 352 and integration operator 354. The decompression controller 350 can extract control data from the header of the compressed data packet to determine the control parameters for decompression operations.

Figure 19:
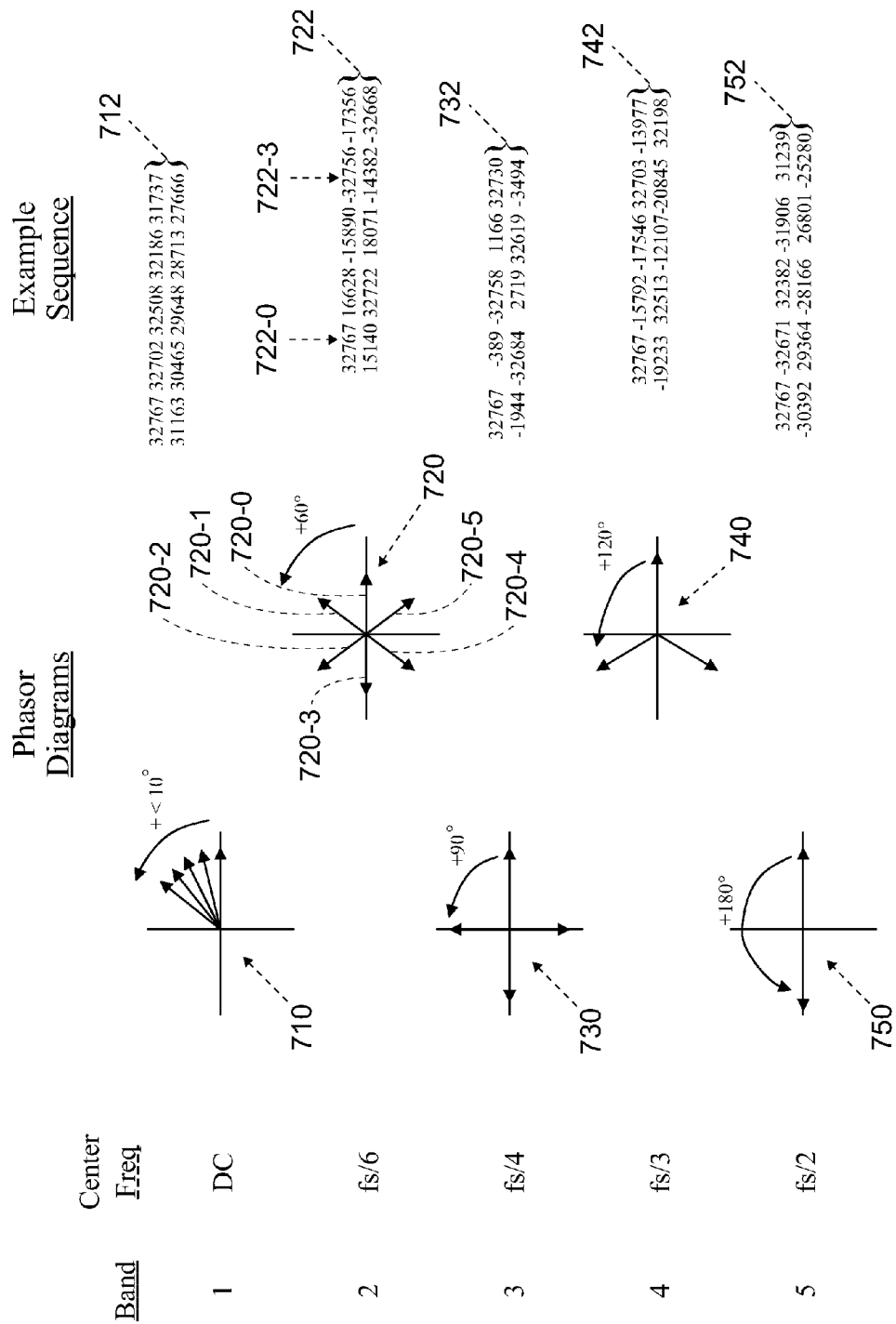
FIG. 19 gives examples that illustrate principles underlying alternatives for compressing signal samples with different center frequencies.

Another alternative for compression applies arithmetic operations to the ultrasound signal samples based on the center frequency and sample rate. FIG. 19 gives examples that illustrate principles underlying alternatives for compressing signal samples with different center frequencies. Beginning with the example of a baseband signal, corresponding to row labeled "Band 1" in FIG. 19, the center frequency is near DC (0 Hz) and the phase increase between consecutive samples is less than 10 degrees. The first phasor diagram 710 shows that since the phase changes between consecutive samples are small, the magnitudes of the differences of consecutive samples will be relatively small compared to the magnitudes of the samples themselves. The first example sequence 712 corresponds to samples of a Band 1 baseband signal. Since the differences between consecutive samples are small relative to the sample magnitudes, calculating first or higher order differences, or differential encoding, creates difference samples with smaller data widths than the original samples. Compression using differential encoding described with respect to FIG. 17 is effective for the baseband (Band 1) example.

FIG. 19 also gives examples of sampled signals where the center frequency is above DC, but below the Nyquist frequency, $f_s/2$. For Band 2, the center frequency is near $f_s/6$ and the phase increase between consecutive samples is about 60 degrees. The second phasor diagram 720 shows that pairs of samples separated by 180 degrees, or three sample intervals, have similar magnitudes but opposite polarities, as illustrated by pairs of samples (720-0, 720-3), (720-1, 720-4) and (720-2, 720-5). Inverting one of the samples in the pair [or multiplying by (−1)] provides a close estimate of the other sample in the pair. The second example sequence 722 also shows that samples separated by three sample intervals have similar magnitudes and opposite signs. For example, the value of sample 722-0 is 32767 and the value of sample 722-3 is −32756. For Band 2, operations on pairs of samples separated by three sample intervals produce modified samples with smaller data widths. The operation of adding the samples in the pair together produces modified samples having smaller data widths that can be encoded more efficiently.

For the example of Band 3 in FIG. 19, the center frequency is near $f_s/4$ and the phase increase between consecutive samples is about 90 degrees. The third phasor diagram 730 shows that samples separated by 180 degrees, or 2 sample intervals, have similar magnitude and opposite polarity. The third example sequence 732 also shows that every other sample has similar magnitudes and opposite polarities. For Band 3, adding together every other sample will result in modified samples with smaller data widths that can be encoded more efficiently than the original samples.

For the example of Band 4 in FIG. 19, the center frequency is near $f_s/3$ and the phase increase between consecutive samples is about 120 degrees. The fourth phasor diagram 740 shows that samples separated by 360 degrees, or 3 sample intervals, will have similar magnitudes. The fourth example sequence 742 shows that every third sample has similar magnitudes. In this case, forming a difference between samples separated by 3 sample intervals will give a modified sample with a smaller data width that can be encoded more efficiently than the original samples.

For the example of Band 5 in FIG. 19, the center frequency is $f_s/2$ and the phase increase between consecutive samples is about 180 degrees. The fifth phasor diagram 750 shows that samples separated by 180 degrees, or one sample interval, will have similar magnitudes but opposite polarities. The fifth example sequence 752 shows consecutive samples have similar magnitudes and opposite polarities. In this case, adding two consecutive samples will form a modified sample with a smaller data width that can be encoded more efficiently than the original samples.

The above examples described for FIG. 19 show that magnitude reduction can be achieved by performing operations such as addition (or inversion followed by subtraction) or subtraction (or inversion followed by addition) on signal samples that are separated by 1, 2 or 3 sample intervals, depending on the ratio of the sample rate to the center frequency. The resulting modified samples are then encoded to form compressed samples. Similar operations can be applied to samples that are separated by four or more sample intervals, depending on the ratio of the center frequency to the sample rate, to produce modified samples with smaller data widths than the original signal samples.

Figure 20:
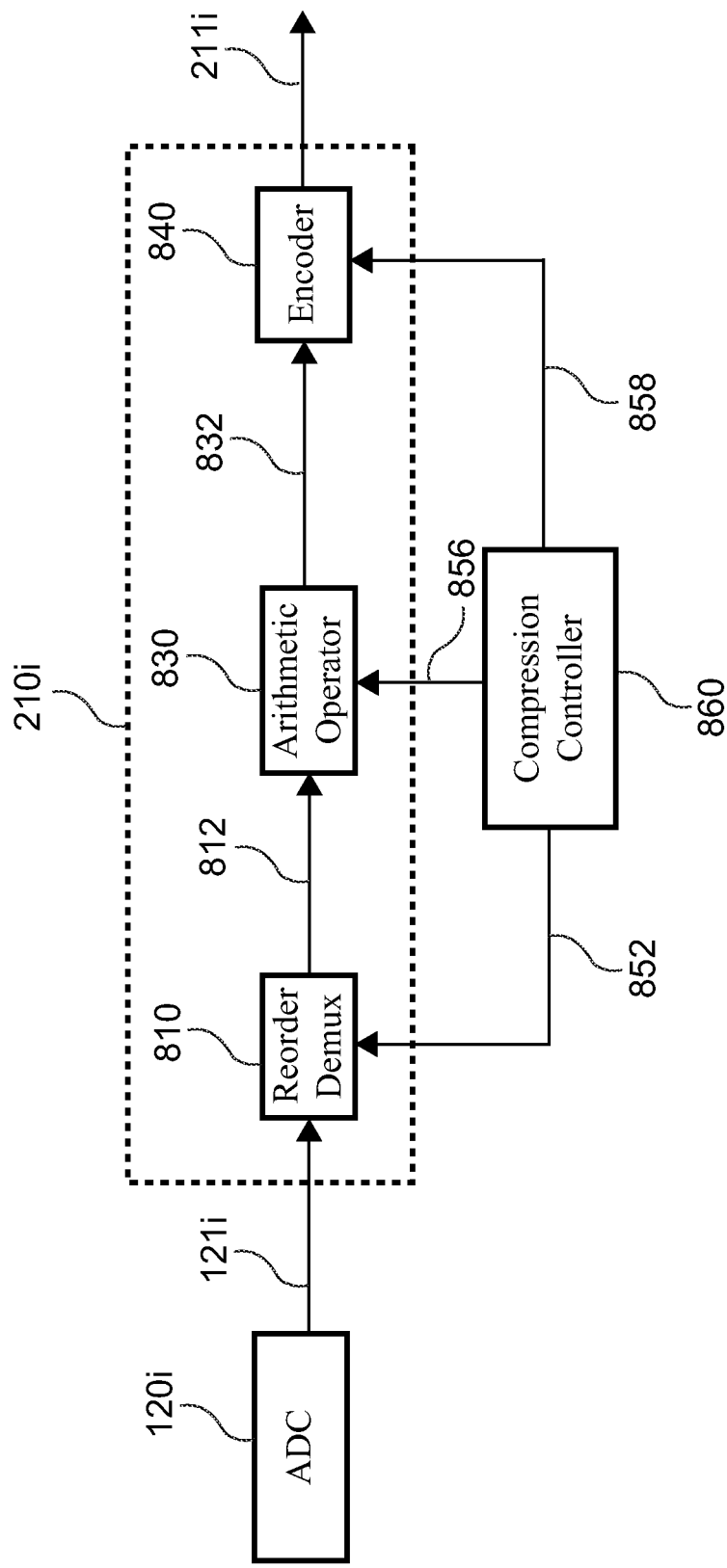
FIG. 20 is a block diagram of the compression algorithm based on the center frequency of the signal samples.

FIG. 20 is a block diagram of the compression algorithm based on the center frequency of the signal samples. The ADC 120*i* provides the ultrasound signal samples to the reorder demux 810. The reorder demux 810 selects signal samples so that selected samples are separated by the appropriate number of sample intervals according to compression control parameter 852 to form demultiplexer output 812. Arithmetic operator 830 performs addition or subtraction operations on pairs of demultiplexer output samples 812 according to compression control parameter 856 to form modified samples 832. Arithmetic operator 830 can also be configured to perform higher order differences on the demultiplexer output samples 812. The encoder 840 encodes the modified samples 832 to form compressed signal samples. The encoder 840 applies block floating point encoding, Huffman encoding or other encoding to form the compressed samples. For block floating point encoding, the modified samples 832 are input to the block floating point encoder instead of the signal samples of the ADC output 121*i*.

The compression controller 860 provides control parameters to the compressor elements based on the ratio of the sample rate to the center frequency of the signal samples. The reorder demux 810 and arithmetic operator 830 respond to the compression control parameters 852 and 856, respectively, to perform the appropriate operations. FIG. 21 shows the operations that produce modified samples 832 based on the center frequency. The first column 871 gives the possible center frequencies for this example. The second column 872 gives a corresponding frequency band indicator for each center frequency. The indicators can be used as parameters for compression controls 852 and 856. The third column 873 gives the different separations of samples x(i) and x(i-j) at reorder demux output 812 that would be produced in accordance with compression control parameter 852. The fourth column 874 shows the result of selecting the arithmetic operations of addition or subtraction in accordance with compression control parameter 856. When the inverter is "on" the delayed sample, x(i-j) is subtracted. The fifth column 875 shows the mathematical results of the arithmetic operator 830 that produce the modified samples 832, or y(i). The compression controller 860 also provides control of the encoder 840. The compression control parameter 858 can indicate a parameter for block floating point encoding or other encoding technique.

FIG. 22 gives the sums or differences of signal samples x(i) and x(i-j) for the examples of FIG. 19 calculated as described with respect to FIGS. 15 and 16 for different center frequencies. The example sequences of signal samples are the same as those of FIG. 19. The samples in the DIFF rows in example sequences 912 and 942 and the SUM rows in example sequences 922, 932 and 952 have substantially lower magnitudes than the corresponding signal samples, or x(i). The DIFF samples and the SUM samples are examples of modified samples 832 that are input to encoder 840 in FIG. 20.

Figure 23:
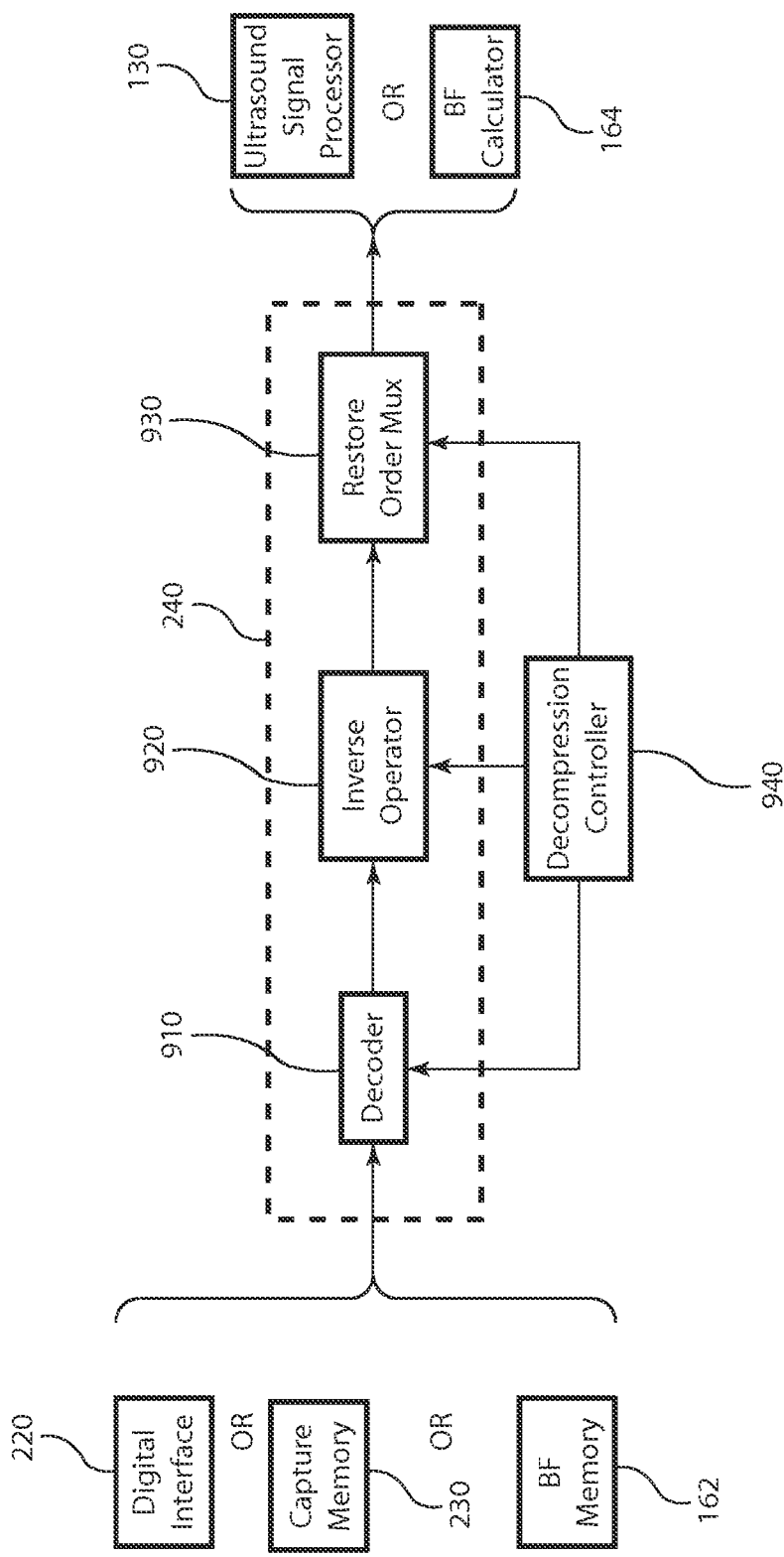
FIG. 23 is a block diagram of the operations performed by the decompressor for the compressor described with respect to FIG. 20.

FIG. 23 is a block diagram of the operations performed by the decompressor 240 for the compressor 210 as described with respect to FIG. 20. The compressed samples are received by the decoder 910 from the digital interface 220, the capture memory 230 or the beamformer memory 162, depending on the system architecture. The decoder 910 unpacks and performs decoding operations, for instance block floating point decoding, on the compressed data, to form decoded modified samples. The inverse arithmetic operator 920 performs the inverse operations to the arithmetic operator 830 to reconstruct the signal samples from the decoded modified samples. The multiplexer 930 restores the original order to the decompressed signal samples to reconstruct the sequence of ultrasound signal samples. The decompression controller 940 provides control parameters to the decoder 910, the inverse operator 920 and the multiplexer 930. The decompression controller 940 can extract control data from the header of the compressed data packet to determine the control parameters for the decompression operations.

The embodiments for the compressor 210 apply simple operations that can compress samples output from the ADCs in real time, or at a rate that is at least as fast as the sample rate. The difference operator 330*i* (FIG. 17) includes one or more subtractors. The block floating point encoding (FIGS. 12 and 16) uses comparators, subtractors and lookup tables. Alternatively, Huffman encoding uses a lookup table to assign a code to a value. The compression operations described with respect to FIG. 20 include demultiplexing, adding and subtracting. The embodiments for the decompressor 240 apply simple operations to decompress the compressed sample. The decompressor 240 includes lookup tables and adders for block floating point decoding. The integration operator 354 (FIG. 18) includes one or more adders for integrating the decoded samples. The operations of the decompressor 240 in FIG. 23 include adding, subtracting and multiplexing.

The preferred implementation of the present invention in an ultrasound system integrates the compressor 210 and the bank of ADCs 120 in a single application specific integrated circuit (ASIC) device. Referring to the block diagram of FIG. 5, the bank of ADCs 120 is integrated with the compressor 210 in a mixed signal integrated circuit device having analog inputs and digital outputs. The plurality of N independent ADCs 120*i* convert N input analog ultrasound signals to N digital ultrasound signals in parallel. The ADCS 120*i* can be implemented by pipeline data converters comprising multiple stages of flash converters or other ADC architecture. Intellectual property (IP) cores for ADCs are commercially available for ASIC implementations. The ADC output channels 121*i* are coupled to digital logic implementing the compressor 210. The preferred implementation of the compressor 210 includes multiple compression cores in parallel, where each compression core is coupled to one of the ADCs 120*i* and implements the compression operations of one compression unit 210*i*. Alternatively, one compression core can implement multiple compression units 210*i* to compress signal samples from more than one ADC 120*i*. For this alternative, the compression core includes buffers to store signal samples from the different ADCs 120*i* until they are processed. The compression operations can also be implemented in a field programmable gate array (FPGA). The compressed samples can be output over LVDS ports 270*i* to the digital interface 220, as shown in FIGS. 8, 9 and 10. The IP cores for LVDS interfaces are commercially available for ASIC and FPGA implementations. Alternative implementations include compression operations in a separate device that is coupled to the outputs of a parallel ADC device. The compression operations can be implemented in an ASIC, FPGA or a programmable processor, such as a digital signal processor (DSP), microprocessor, microcontroller, multi-core CPU (such as IBM Cell), or graphics processing unit (GPU; such as Nvidia GeForce).

Depending on the ultrasound system architecture, the decompressor 240 may be incorporated into the same device as or a different device from the ultrasound signal processor 130. The decompression operations can be implemented in an ASIC or FPGA. Alternatively, the decompression operations can be implemented in software or firmware programs executable by a programmable processor, such as a DSP, microprocessor, microcontroller, CPU or GPU. The preferred implementation of the decompressor 240 is a software program having instructions for the decompression operations executable by a GPU. The GPU may also be programmed to implement at least a portion of the operations, such as beamforming operations, of the ultrasound signal processor 130 on the decompressed samples. Alternatively, the decompressed samples may be transferred to another programmable processor, such as a CPU, for the ultrasound signal processing operations.

Figure 24:
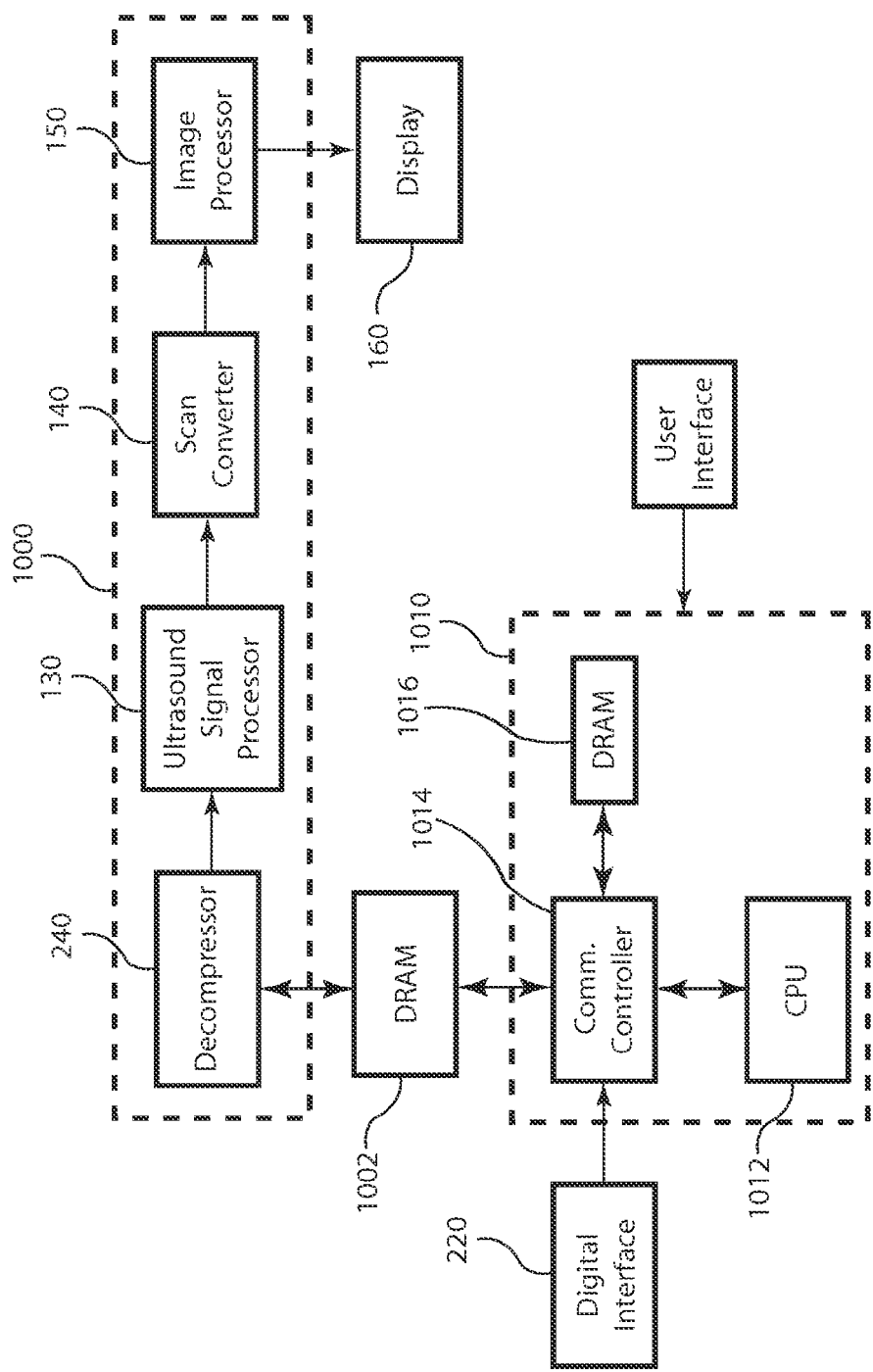
FIG. 24 is a block diagram of an implementation in a GPU of the decompressor and the other operations for generating an ultrasound image.

FIG. 24 is a block diagram of an implementation in a GPU of the decompressor 240 and the other operations for generating an ultrasound image. Current GPU architectures include multiple processing cores optimized for parallel calculations. For example, the Nvidia GeForce GTS 150 GPU includes 128 processing cores. Nvidia's "CUDA" (Compute Unified Device Architecture) is an application programming interface (API) that includes extensions to the C language for implementing parallel algorithms on the GPU's processing cores and is described in the document entitled "Getting Started with CUDA" by Ruetsch and Oster, Nvidia Corp., 2008. Alternative GPU and programming methodologies, such as OpenCL and Larrabee, described below, may provide the implementation platform. For the implementation depicted in FIG. 24, the GPU device 1000 may be programmed to execute the operations of the decompressor 240, the ultrasound signal processor 130 (beamforming, B-mode processing and Doppler processing), the scan converter 140 and the image processor 150. The GPU device 1000 may include a dynamic random access memory (DRAM) 1002 accessible by the parallel processing units. The DRAM 1002 may store compressed and/or decompressed samples and data resulting from the GPU's other processing operations. The system controller 1010 provides coordination of tasks for generating the ultrasound image from received data and responds to the user commands. The CPU 1012 may implement operations in support of decompression, such as decoding compression control parameters from the headers of compressed packets and providing them to the GPU device 1000 for configuring the decompression operations. The DRAM 1016 may store compressed samples received from the digital interface 220 and other data needed for the CPU operations. The communication controller 1014 directs the compressed packets received from the digital interface 220 to the DRAM 1002 or the DRAM 1016 and manages data exchange between the system controller 1010 and the GPU device 1000.

In a preferred system architecture, the system controller 1010 may be embodied in a motherboard of a computer having a screen for the display 160. The GPU device 1000 may be embodied in a graphics card, including the DRAM 1002, in communication with the system controller 1010 by a PCIe (Peripheral Component Interconnect Express) backplane link. Alternatively, the GPU device 1000 may be embodied in an IC mounted on the motherboard. In a system architecture where the ADC bank 120 and compressor 210 are mounted in a data acquisition card, the digital interface 220 may be embodied by a PCIe backplane link.

It will be appreciated that, in accordance with Moore's Law, higher levels of integration will provide for more compact devices so that the system controller 1010 and the GPU device 1000 may be implemented in a single IC. For example, Intel Corporation is developing a many-core IC architecture that includes multiple instantiations of an x86 CPU core augmented with a vector processing unit. The architecture, referred to as Larrabee, is described in the document entitled "Larrabee: A Many-Core x86 Architecture for Visual Computing" by Seiler et al., ACM Transactions on Graphics, Vol. 27, No. 3, Article 18, August 2008. The Larrabee architecture supports applications requiring parallel processing, including graphics processing. The "Larrabee Native" programming model includes a C/C++ and APIs for parallel programming and vectorization.

Figure 25:
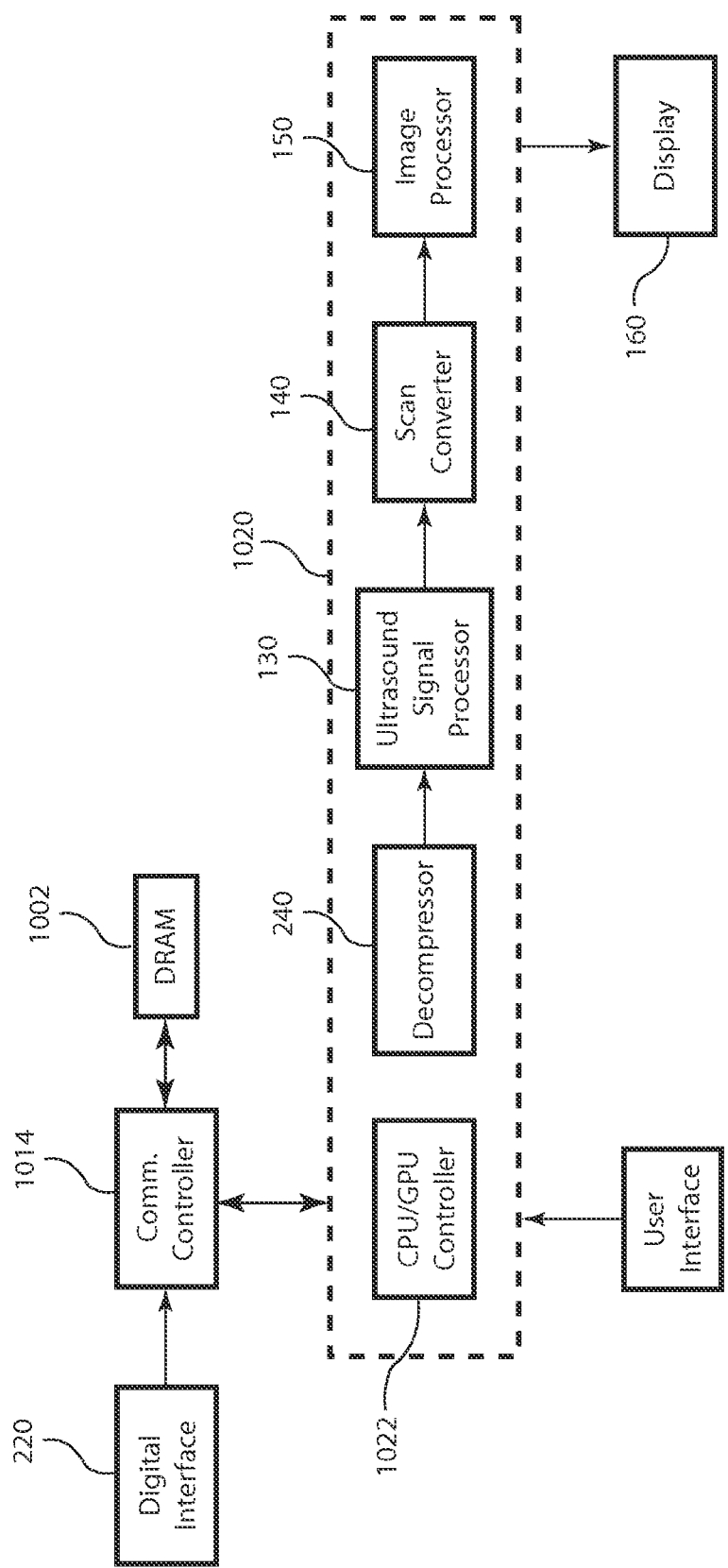
FIG. 25 is a block diagram of an implementation in a CPU/GPU device of the decompressor and the other operations for generating an ultrasound image.

FIG. 25 is a block diagram of an implementation in a CPU/GPU device of the decompressor 240 and the other operations for generating an ultrasound image. The CPU/GPU device 1020 may implement the operations of the decompressor 240, the ultrasound signal processor 130, the scan converter 140 and the image processor 150. The CPU/GPU controller 1022 coordinates the processing operations on the compressed samples received from the digital interface 220 and responds to user input. The CPU/GPU device 1020 may be implemented by the Larrabee platform or other programmable device with integrated CPU and GPU functionality.

In a system architecture where the ADC bank 120 and compressor 210 are housed in the transducer head, the digital interface 220 may be a wired or a wireless communication link. For a wired communication link, the digital interface may be implemented by a PCIe cable link or an optical fiber link. For a wireless communication link, the digital interface may provide digital modulation and transmission of the compressed packets via a radio frequency channel and digital demodulation of the received compressed packets. The wireless link may comply with a wireless communication protocol, such as WiFi (IEEE 802.11) or an UWB (ultra-wideband) format.

While the preferred embodiments of the invention have been illustrated and described, it will be clear that the invention is not limited to these embodiments only. Numerous modifications, changes, variations, substitutions and equivalents will be apparent to those skilled in the art, without departing from the spirit and scope of the invention, as described in the claims.

We claim:

1. In an ultrasound imaging system including an array of N ultrasound transducer elements that outputs N analog ultrasound signals during a sampling window, a method comprising:
digitally sampling the N analog ultrasound signals in parallel using N analog to digital converters (ADCs) to produce N sequences of signal samples during the sampling window, each ADC sampling a corresponding analog ultrasound signal output by a corresponding transducer element to form a corresponding sequence of signal samples, each signal sample represented by a number of bits per sample;

multiplexing the N sequences of signal samples to M channels of multiplexed signal samples where M is less than N by mapping the bits of the N signal samples for each sample period to M subsets of bits, where each subset of bits is provided to a corresponding on of the M channels; and transferring the M channels of multiplexed signal samples over M data ports across a data transfer interface to a signal processor.

2. The method of claim 1, further comprising:

receiving the M channels of multiplexed signal samples at the signal processor; and demultiplexing the M channels of multiplexed signal samples to form N reproduced sequences of signal samples by demapping the M subsets of bits to reproduce the N signal samples for each sample period, wherein the N reproduced sequences of signal sample are processed by the signal processor.

3. For use in an ultrasound imaging system including an array of N ultrasound transducer elements that outputs N analog ultrasound signals during a sampling window, an apparatus comprising:

an integrated circuit device having N analog inputs for receiving the N analog ultrasound signals and n data ports at a digital interface, the integrated circuit device comprising:

N analog to digital converters (ADCs) coupled to digitally sample the N analog ultrasound signals received at the analog inputs to produce N sequences of signal samples during the sampling window, each ADC sampling a corresponding analog ultrasound signal to form a corresponding sequence of signal samples, each signal sample represented by a number of bits per sample; and a multiplexer having N inputs coupled to receive the N sequences of signal samples and producing M channels of multiplexed signal samples, where M is less than N, the multiplexer mapping the bits of the N signal samples for each sample period to M subsets of bits, wherein each subset of bits is provided to a corresponding one of the M channels for transfer over M of the N data ports at the digital interface to the signal processor.

4. The apparatus of claim 3, further comprising:

a demultiplexer coupled to receive the M channels of multiplexed signal samples from the digital interface, wherein the demultiplexer demaps the M subsets of bits to reproduce the N signal samples for each sample period and provides N reproduced sequences of signal samples to the signal processor.

* * * * *